US009080861B2

(12) United States Patent
Yamauchi et al.

(10) Patent No.: US 9,080,861 B2
(45) Date of Patent: Jul. 14, 2015

(54) OBSERVATION DEVICE, AND OBSERVATION METHOD

(75) Inventors: Toyohiko Yamauchi, Hamamatsu (JP); Hidenao Iwai, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 996 days.

(21) Appl. No.: 13/059,860

(22) PCT Filed: Aug. 19, 2009

(86) PCT No.: PCT/JP2009/064520
§ 371 (c)(1),
(2), (4) Date: May 2, 2011

(87) PCT Pub. No.: WO2010/021343
PCT Pub. Date: Feb. 25, 2010

(65) Prior Publication Data
US 2011/0205547 A1    Aug. 25, 2011

(30) Foreign Application Priority Data

Aug. 20, 2008  (JP) ................. P2008-211990
Aug. 20, 2008  (JP) ................. P2008-212004

(51) Int. Cl.
*G01B 11/02*  (2006.01)
*G01B 11/24*  (2006.01)
*G01N 21/45*  (2006.01)

(52) U.S. Cl.
CPC ............ *G01B 11/2441* (2013.01); *G01N 21/45* (2013.01)

(58) Field of Classification Search
CPC ........... G01B 9/02062; G01B 9/02064; G01B 9/02065; G01B 9/02071
USPC ......................... 356/496, 497, 511
See application file for complete search history.

(56) References Cited

U.S. PATENT DOCUMENTS 4,818,108 A * 4/1989 Eppinger ................ 356/513
7,486,406 B2 * 2/2009 Kim ...................... 356/497
(Continued)

FOREIGN PATENT DOCUMENTS

JP       09-218016       8/1997
JP    2001212086 A  *  8/2001
(Continued)

OTHER PUBLICATIONS

Isao Takahashi et al., "Displacement Measurement of Object with Step Using Phase-shifting Digital Holography", Nippon Jikkenryoku Gakkai Koen Ronbunshu, 2003, No. 3, pp. 89 to 91, with English abstract.

*Primary Examiner* — Tarifur Chowdhury
*Assistant Examiner* — Jonathon Cook
(74) *Attorney, Agent, or Firm* — Drinker Biddle & Reath LLP

(57) ABSTRACT

The observation device 1 is to observe the surface or the inside of an observation object 9, that has light sources 11 and 12, lenses 21 to 25, an aperture 31, an optical multiplexer 41, an optical demultiplexer 42, a half mirror 43, an image pickup unit 51, an analyzing unit 52, a display unit 53, a light receiving unit 61, a displacement detecting unit 62, a piezoelectric actuator 71, a drive unit 72, a mirror 73, a stage 81, a drive unit 82, and a control unit 90. The analyzing unit 52 determines a complex amplitude of an interference light figure taken as an image by the image pickup unit 51 with a phase shift technique after an optical path difference is set to each target value in sequence, and determines an amount of change per certain time of a phase component of a reflected light generated on the surface or the inside of the observation object 9 on the basis of an absolute value of an amount of change per certain time of the determined complex amplitude and an absolute value of the complex amplitude.

10 Claims, 27 Drawing Sheets

(56) References Cited

U.S. PATENT DOCUMENTS 8,077,324 B2 * 12/2011 Xiangqian et al. ............ 356/511
2002/0135777 A1 * 9/2002 Ge ................................. 356/511
2009/0015844 A1 * 1/2009 De Groot ...................... 356/511

FOREIGN PATENT DOCUMENTS

| JP | 2004-028647 | 1/2004 |
| JP | 2005-182143 | 7/2005 |
| JP | 2006-084304 | 3/2006 |
| JP | 2009-008393 | 1/2009 |

* cited by examiner

Fig.26
(a)
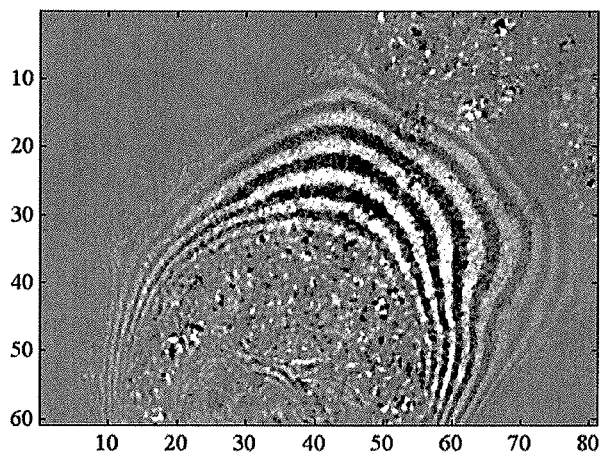
(b)
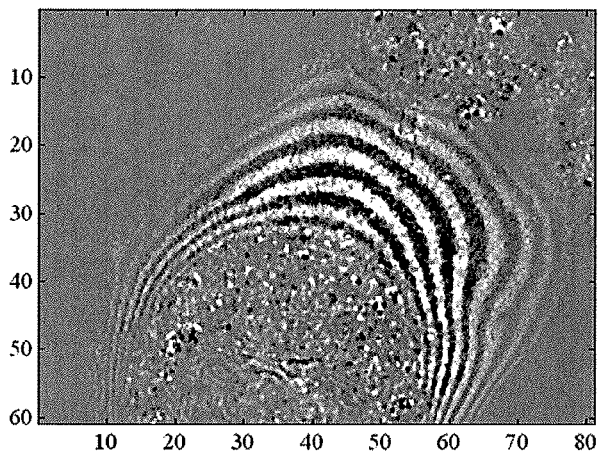
(c)
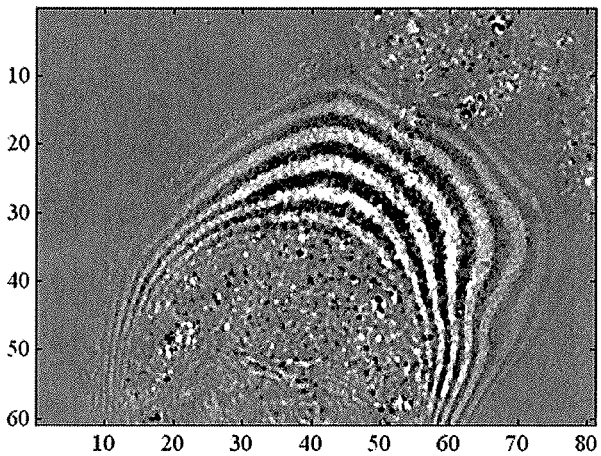

*Fig.27*
(a)
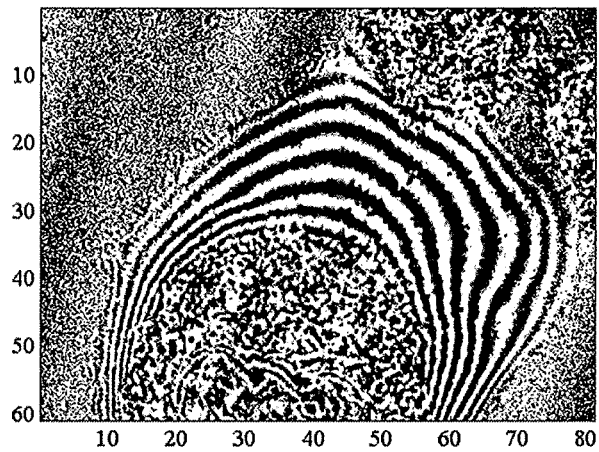
(b)
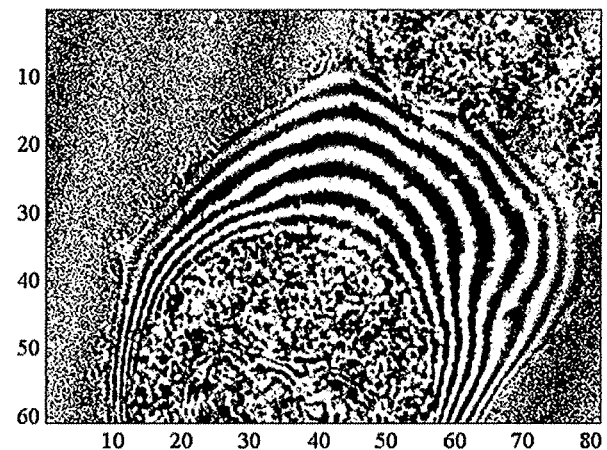
(c)
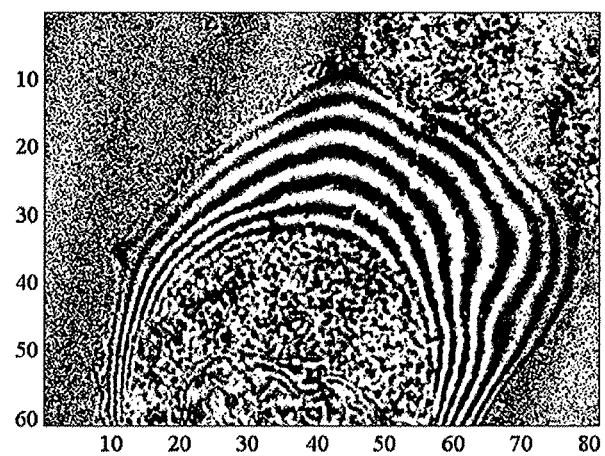

OBSERVATION DEVICE, AND OBSERVATION METHOD

TECHNICAL FIELD

The present invention relates to a method and a device for observing an observation object.

BACKGROUND ART

As a device for observing or measuring an object by using an interference optical system, a device has been known which is disclosed in Patent Literature 1. The device disclosed in this literature observes or measures an object on the basis of the amplitude peak of interference fringes by utilizing that the amplitude peak of interference fringes due to a reflected light from an object and a reflected light from a mirror depends on an optical path difference.

CITATION LIST

Patent Literature

Patent Literature 1: Japanese Unexamined Patent Application Publication No. H9-218016

SUMMARY OF INVENTION

Technical Problem

However, the device disclosed in Patent Literature 1 is incapable of obtaining detailed information on an object such as a cell. The present invention has been achieved in order to solve the above-described problem, and it is an object of the present invention to provide an observation device and an observation method which are capable of obtaining detailed information on an object such as a cell.

Further, the device disclosed in Patent Literature 1 is incapable of effectively displaying information. The present invention has been achieved in order to solve the above-described problem, and it is an object of the present invention to provide an observation device and an observation method which are capable of obtaining detailed information on an object such as a cell to effectively display the information.

Solution to Problem

An observation device according to the present invention includes: (1) a light source which outputs light; (2) an interference optical system which branches the light output from the light source into two to output as a first branched light and a second branched light, inputs a first reflected light generated due to the first branched light being reflected by a mirror, inputs a second reflected light generated due to the second branched light being reflected by a surface or an inside of an observation object, and causes the first reflected light and the second reflected light to interfere with each other to output an interference light; (3) an imaging optical system which images the interference light output from the interference optical system; (4) an image pickup unit which takes an image of an interference light figure imaged by the imaging optical system; (5) optical path difference adjusting means for adjusting an optical path difference between an optical path length from the light source via a reference position of the observation object up to the image pickup unit and an optical path length from the light source via the mirror up to the image pickup unit; and (6) a control unit which controls an optical path difference adjusting operation by the optical path difference adjusting means such that the optical path difference becomes each target value in sequence.

The observation device according to the present invention further includes an analyzing unit which determines a complex amplitude of the interference light figure taken as an image by the image pickup unit with a phase shift technique after the optical path difference is set to each target value in sequence by the optical path difference adjusting means, and determines an amount of change per certain time of a phase component of the second reflected light generated on the surface or the inside of the observation object on the basis of an absolute value of an amount of change per certain time of the determined complex amplitude and an absolute value of the complex amplitude.

An observation method according to the present invention, which uses a light source, an interference optical system, an imaging optical system, an image pickup unit, optical path difference adjusting means, and a control unit as described above, includes: determining a complex amplitude of the interference light figure taken as an image by the image pickup unit with a phase shift technique after the optical path difference is set to each target value in sequence by the optical path difference adjusting means; and determining an amount of change per certain time of a phase component of the second reflected light generated on the surface or the inside of the observation object on the basis of an absolute value of an amount of change per certain time of the determined complex amplitude and an absolute value of the complex amplitude.

It is preferable that the observation device according to the present invention further includes a display unit which displays an image of a spatial distribution of an amount of change per certain time of a phase component of the second reflected light determined by the analyzing unit. It is preferable that the observation method according to the present invention further includes displaying an image of a spatial distribution of an amount of change per certain time of a phase component of the second reflected light by a display unit.

It is preferable that, in the observation device according to the present invention, the analyzing unit determines an amount of change per certain time of a phase component of the second reflected light with respect to each of a plurality of sliced planes of the observation object. It is preferable that the observation method according to the present invention includes determining an amount of change per certain time of a phase component of the second reflected light with respect to each of a plurality of sliced planes of the observation object.

It is preferable that the observation device according to the present invention further includes optical path difference detecting means for detecting the optical path difference, in which the optical path difference adjusting means adjusts the optical path difference on the basis of detected results by the optical path difference detecting means.

It is preferable that the observation method according to the present invention, which further uses optical path difference detecting means for detecting the optical path difference, includes adjusting the optical path difference by the optical path difference adjusting means on the basis of detected results by the optical path difference detecting means.

It is preferable that, in the observation device or the observation method according to the present invention, (a) the optical path difference adjusting means includes first moving means for moving a first object which is one of the observation object and the mirror, and second moving means for moving a second object which is the other one of the observation object and the mirror, the optical path difference adjusting means adjusting the optical path difference by a moving operation by the first moving means or the second moving means, (b) the first moving means has an operating range narrower than an operating range of the second moving means, and has a positional accuracy higher than a positional accuracy of the second moving means, (c) the second moving means moves the second object so as to maintain the optical system between the interference optical system and the second object, and (d) the control unit causes a moving operation by the second moving means to be continuously or intermittently performed such that an amount of moving by the first moving means falls within a predetermined range within the operating range at each target value of the optical path difference, and performs feedback control of a moving operation by the first moving means such that the optical path difference becomes each target value even at the time of the moving operation by the second moving means.

It is preferable that, in the observation device or the observation method according to the present invention, the observation object includes a cell.

An observation device according to the present invention includes: (1) a light source which outputs light; (2) an interference optical system which branches the light output from the light source into two to output as a first branched light and a second branched light, inputs a first reflected light generated due to the first branched light being reflected by a mirror, inputs a second reflected light generated due to the second branched light being reflected by a surface or an inside of an observation object, and causes the first reflected light and the second reflected light to interfere with each other to output an interference light; (3) an imaging optical system which images the interference light output from the interference optical system; (4) an image pickup unit which takes an image of an interference light figure imaged by the imaging optical system; (5) optical path difference adjusting means for adjusting an optical path difference between an optical path length from the light source via a reference position of the observation object up to the image pickup unit and an optical path length from the light source via the mirror up to the image pickup unit; and (6) a control unit which controls an optical path difference adjusting operation by the optical path difference adjusting means such that the optical path difference becomes each target value in sequence.

The observation device according to the present invention further includes: (7) an analyzing unit which determines an intensity component and a phase component of the second reflected light generated on the surface or the inside of the observation object with a phase shift technique on the basis of the interference light figure taken as an image by the image pickup unit after the optical path difference is set to each target value in sequence by the optical path difference adjusting means; and (8) a display unit which displays an image of the second reflected light in an HSV color space such that the phase component of the second reflected light determined by the analyzing unit is reflected to hue, and the intensity component of the second reflected light determined by the analyzing unit is reflected to saturation or value.

An observation method according to the present invention, which uses a light source, an interference optical system, an imaging optical system, an image pickup unit, optical path difference adjusting means, and a control unit as described above, includes: determining an intensity component and a phase component of the second reflected light generated on the surface or the inside of the observation object with a phase shift technique on the basis of the interference light figure taken as an image by the image pickup unit after the optical path difference is set to each target value in sequence by the optical path difference adjusting means; and displaying an image of the second reflected light in an HSV color space such that the determined phase component of the second reflected light is reflected to hue, and the determined intensity component of the second reflected light is reflected to saturation or value.

It is preferable that, in the observation device according to the present invention, the analyzing unit determines plural sets of intensity components and phase components of the second reflected lights in time-series, and the display unit displays images of these second reflected lights in time-series in the HSV color space on the basis of the plural sets of intensity components and phase components of the second reflected lights determined by the analyzing unit. It is preferable that the observation method according to the present invention includes: determining plural sets of intensity components and phase components of the second reflected lights in time-series; and displaying images of these second reflected lights in the HSV color space in time-series on the basis of these determined plural sets of intensity components and phase components of the second reflected lights.

It is preferable that, in the observation device according to the present invention, the analyzing unit determines an intensity component and a phase component of the second reflected light with respect to each of a plurality of sliced planes of the observation object, and the display unit displays images of these second reflected lights in the HSV color space on the basis of plural sets of intensity components and phase components of the second reflected lights determined by the analyzing unit. It is preferable that the observation method according to the present invention includes: determining an intensity component and a phase component of the second reflected light with respect to each of a plurality of sliced planes of the observation object; and displaying images of these second reflected lights in the HSV color space on the basis of these determined plural sets of intensity components and phase components of the second reflected lights.

It is preferable that the observation device according to the present invention further includes optical path difference detecting means for detecting the optical path difference, in which the optical path difference adjusting means adjusts the optical path difference on the basis of detected results by the optical path difference detecting means. It is preferable that the observation method according to the present invention, which further uses optical path difference detecting means for detecting the optical path difference includes adjusting the optical path difference by the optical path difference adjusting means on the basis of detected results by the optical path difference detecting means.

It is preferable that, in the observation device or the observation method according to the present invention, (a) the optical path difference adjusting means includes first moving means for moving a first object which is one of the observation object and the mirror, and second moving means for moving a second object which is the other one of the observation object and the mirror, the optical path difference adjusting means adjusting the optical path difference by a moving operation by the first moving means or the second moving means, (b) the first moving means has an operating range narrower than an operating range of the second moving means, and has a positional accuracy higher than a positional accuracy of the second moving means, (c) the second moving means moves the second object so as to maintain the optical system between the interference optical system and the second object, and (d) the control unit causes a moving operation by the second moving means to be continuously or intermittently performed such that an amount of moving by the first moving means falls within a predetermined range within the operating range at each target value of the optical path difference, and performs feedback control of a moving operation by the first moving means such that the optical path difference becomes each target value even at the time of the moving operation by the second moving means.

It is preferable that, in the observation device or the observation method according to the present invention, the observation object includes a cell.

ADVANTAGEOUS EFFECTS OF INVENTION

According to the present invention, it is possible to obtain detailed information on an object such as a cell. Further, according to the present invention, it is possible to obtain detailed information on an object such as a cell to effectively display the information.

BRIEF DESCRIPTION OF DRAWINGS

FIGS. 26 are charts shown such that the image shown in FIG. 24 (the image originally displayed in false color) is decomposed into the respective components of R, G, and B.

FIGS. 27 are charts shown such that the image shown in FIG. 25 (the image originally displayed in false color) is decomposed into the respective components of R, G, and B.

REFERENCE SIGNS LIST

Figure 1:
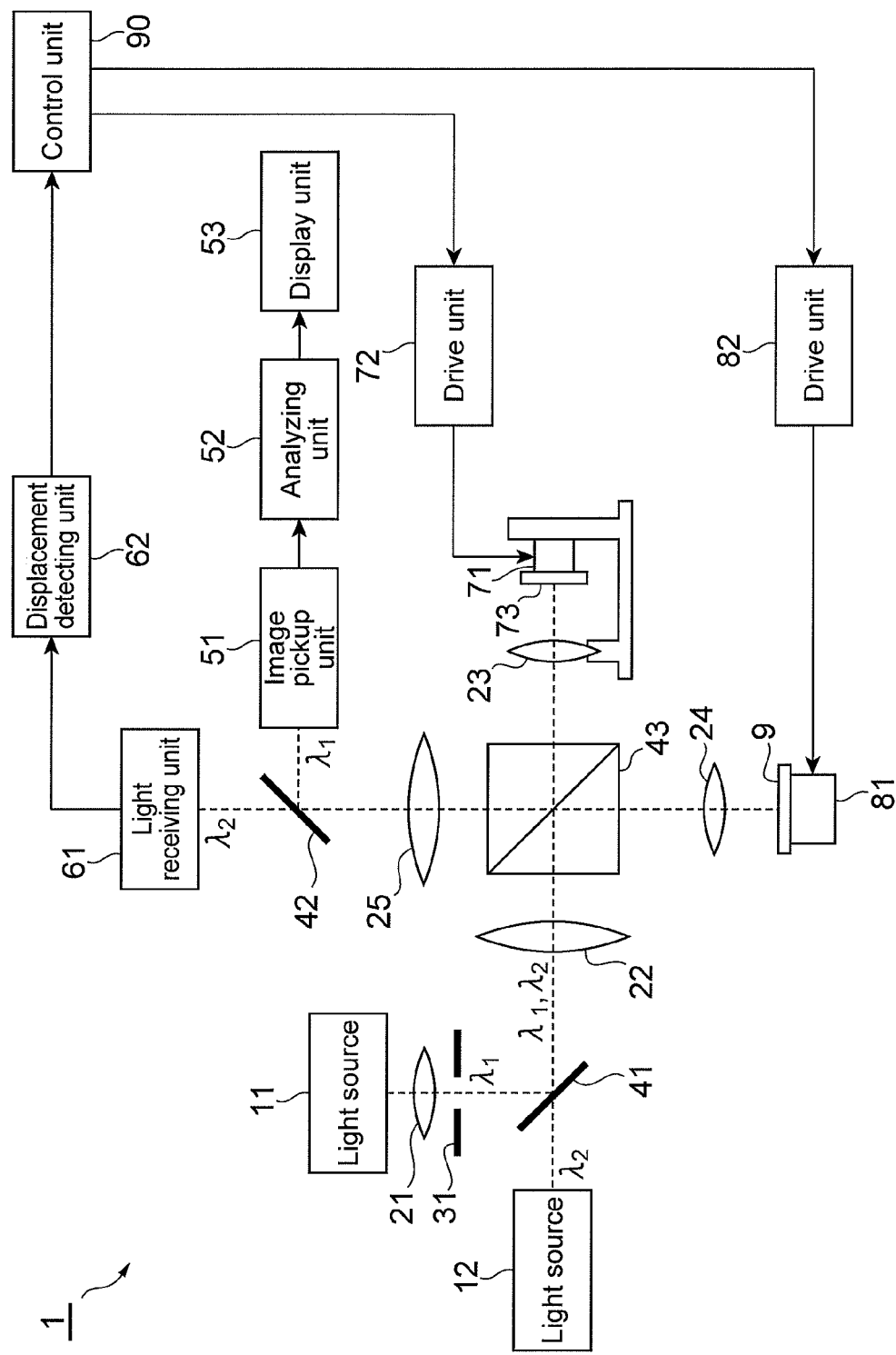
FIG. 1 is a block diagram of an observation device 1 according to an embodiment.

1 . . . observation device, 9 . . . observation object, 11, 12 . . . light sources, 21 to 25 . . . lenses, 31 . . . aperture, 41 . . . optical multiplexer, 42 . . . optical demultiplexer, 43 . . . half mirror, 51 . . . image pickup unit, 52 . . . analyzing unit, 53 . . . display unit, 61 . . . light receiving unit, 62 . . . displacement detecting unit, 71 . . . piezoelectric actuator, 72 . . . drive unit, 73 . . . mirror, 81 . . . stage, 82 . . . drive unit, 90 . . . control unit.

DESCRIPTION OF EMBODIMENTS

Hereinafter, the best modes for carrying out the present invention will be described in detail with reference to the accompanying drawings. In addition, components which are the same in the description of the drawings are denoted by the same reference numerals, and overlapping descriptions thereof will be omitted.

(Entire configuration of observation device 1)

FIG. 1 is a block diagram of an observation device 1 according to this embodiment. The observation device 1 shown in the drawing is to observe the surface or the inside of an observation object 9, which has light sources 11 and 12, lenses 21 to 25, an aperture 31, an optical multiplexer 41, an optical demultiplexer 42, a half mirror 43, an image pickup unit 51, an analyzing unit 52, a display unit 53, a light receiving unit 61, a displacement detecting unit 62, a piezoelectric actuator 71, a drive unit 72, a mirror 73, a stage 81, a drive unit 82, and a control unit 90.

The light source 11 is to output a light $\lambda_1$ having relatively short coherence length, which is, for example, a tungsten lamp capable of outputting a broadband light of a wavelength band range of 600 nm to 900 nm. The coherence length of the light $\lambda_1$ output from the light source 11 is preferably less than or equal to 5 μm. On the other hand, the light source 12 is to output a light $\lambda_2$ having relatively long coherence length, which is, for example, a semiconductor laser light source outputting a laser light at a wavelength of 1.31 μm. The optical multiplexer 41 reflects the light $\lambda_1$ output from the light source 11 to reach there via the lens 21 and the aperture 31, and allows the light $\lambda_2$ output from the light source 12 to reach there to penetrate therethrough, and multiplexes these lights to output it to the lens 22.

The half mirror 43 branches the lights $\lambda_1$ and $\lambda_2$ multiplexed by the optical multiplexer 41 to reach there via the lens 22 into two as a first branched light and a second branched light, and outputs the first branched light to the lens 23 and outputs the second branched light to the lens 24. Further, the half mirror 43 causes a first reflected light generated such that the first branched light passes through the lens 23 to be reflected by the mirror 73, to pass through the lens 23 to be again input thereto, and causes a second reflected light generated such that the second branched light passes through the lens 24 to be reflected by the surface or the inside of the observation object 9, to pass through the lens 24 to be again input thereto. Then, the half mirror 43 causes these first reflected light and second reflected light to interfere with each other, and outputs the interference light to the lens 25. That is, the half mirror 43 is an element composing the interference optical system.

The optical demultiplexer 42 allows the lights output from the half mirror 43 to pass through the lens 25 to be input thereto, and reflects the light $\lambda_1$ of the lights to output the light $\lambda_1$ to the image pickup unit 51, and allows the light $\lambda_2$ to penetrate therethrough to output the light $\lambda_2$ to the light receiving unit 61. The lenses 23 to 25 are elements composing an imaging optical system which images the interference light $\lambda_1$ output from the half mirror 43 to be demultiplexed by the optical demultiplexer 42 on the image pickup surface of the image pickup unit 51. The image pickup unit 51 is to take an image of the imaged interference light $\lambda_1$, and is, for example, a CCD camera. The light receiving unit 61 is to detect the intensity of the light $\lambda_2$ output from the half mirror 43 to be demultiplexed by the optical demultiplexer 42, and is, for example, a photodiode.

Here, an optical path difference between an optical path length from the half mirror 43 to be reflected by the mirror 73 to again reach the half mirror 43 and an optical path length from the half mirror 43 to be reflected at a reference position of the observation object 9 to again reach the half mirror 43, is set to $\Delta L$. In addition, the reference position of the observation object 9 may be the highest position of the observation object 9 (the position nearest the lens 24), a board on which the observation object 9 is placed, the intermediate position therebetween, or another position.

Figure 2:
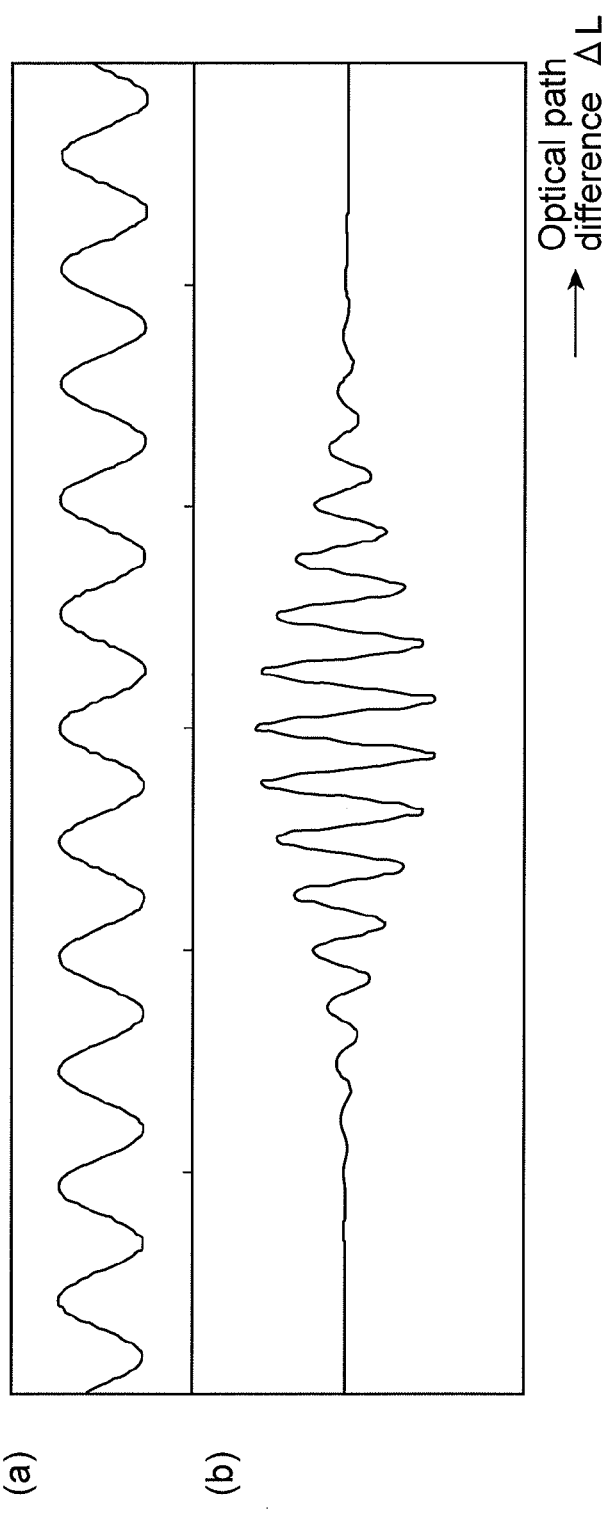
FIG. 2 is a diagram showing the relationship between intensities of lights reaching an image pickup unit 51 or a light receiving unit 61 and an optical path difference.

As described above, the coherence length of the light $\lambda_2$ output from the light source 12 to reach the light receiving unit 61 is relatively long. Therefore, as shown in FIG. 2A, the intensity of the light $\lambda_2$ reaching the light receiving unit 51 changes periodically within a range of a relatively broad optical path difference $\Delta L$. On the other hand, the coherence length of the light $\lambda_1$ output from the light source 11 to reach the image pickup unit 51 is relatively short. Therefore, as shown in FIG. 2B, the intensity of the light $\lambda_1$ reaching the image pickup unit 61 changes periodically within a range of a relatively narrow optical path difference $\Delta L$, and in addition, the more approximate the optical path difference $\Delta L$ to value 0, the greater the amplitude of the interference is.

With this, the analyzing unit 52 acquires an interference light figure of the light $\lambda_1$ taken as an image by the image pickup unit 51 when a optical path difference is set to each of a plurality of target values. This interference light figure is a figure due to the interference between the first reflected light generated by the mirror 73 and the second reflected light generated by the sliced plane (and in a range of approximately the coherence length of the light $\lambda_1$ centering on the sliced plane) when an optical path length from the half mirror 43 to the mirror 73 and an optical path length from the half mirror 43 to a certain sliced plane of the observation object 9 are substantially equal to each other. Moreover, the analyzing unit 52 performs a predetermined analysis on the basis of the acquired interference light figure. The display unit 53 displays an image of the result of the analysis by the analyzing unit 52. The analysis by the analyzing unit 52 and the image display by the display unit 53 will be described later.

Figure 3:
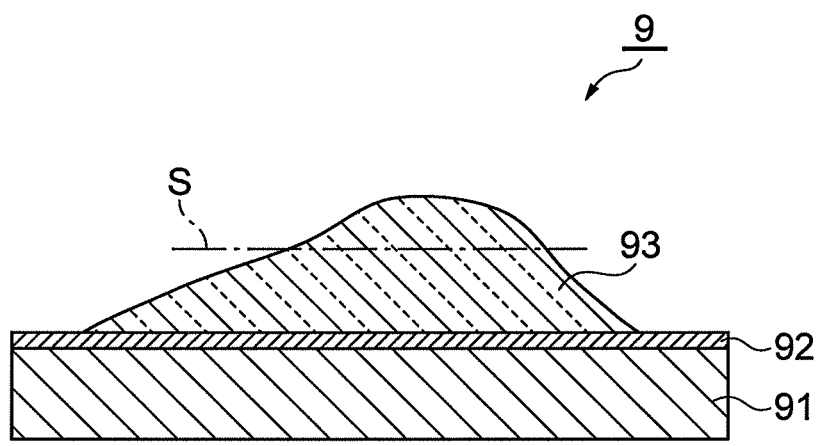
FIG. 3 is a diagram showing a configuration example of an observation object 9.

The observation object 9 is preferably, for example, as shown in FIG. 3, a semitransparent cell 93 placed on a thin membrane 92 formed on the principal surface of a substantially flat substrate 91. The thin membrane 92 reflects the light $\lambda_2$ at high reflectance, so that the thin membrane 92 is suitable for use as a reference plane at the time of feedback control which will be described later. A sliced plane S is set as a cross section of the cell 93 serving as the observation object 9. This sliced plane S is a plane vertical to the optical axis of the lens 24, and is variable in position in the optical axis direction.

The displacement detecting unit 62 determines an optical path difference (or an amount of change in optical path difference with respect to a certain reference value) on the basis of a change in intensity of the light $\lambda_2$ detected by the light receiving unit 61. That is, the light source 12, the light receiving unit 61, and the displacement detecting unit 62 are elements composing optical path difference detecting means for detecting an optical path difference. In addition, a minute vibration is applied to the mirror 73 by the piezoelectric actuator 71, to modulate mainly a certain optical path difference, which makes it possible to more precisely detect the optical path difference.

The piezoelectric actuator 71, the drive unit 72, the stage 81, and the drive unit 82 are elements composing optical path difference adjusting means for adjusting an optical path difference. The piezoelectric actuator 71 is driven by the drive unit 72 to move the mirror 73 in a direction parallel to the optical axis of the optical system between the half mirror 43 and the mirror 73. At this time, the optical system between the half mirror 43 and the mirror 73 is maintained without moving the lens 23. The focal plane of the lens 23 is matched to the reflection plane of the mirror 73 at an accuracy of a focal depth (for example, 0.5 μm).

The stage 81 is driven by the drive unit 82 to move the observation object 9 in a direction parallel to the optical axis of the optical system between the half mirror 43 and the observation object 9. At this time, the optical system between the half mirror 43 and the observation object 9 is maintained without moving the lens 24. That is, the distance to the focal plane on the observation object 9 side measured from the half mirror 43 is maintained.

The operating range of the piezoelectric actuator 71 (first moving means) is narrower than the operating range of the stage 81 (second moving means). Further, the positional accuracy of the piezoelectric actuator 71 is higher than the positional accuracy of the stage 81. In addition, as the drive unit 82 for moving the stage 81, for example, a long-distance moving type piezoelectric actuator or a rotating mechanism by a stepping motor may be used.

The control unit 90 controls an optical path difference adjusting operation by the piezoelectric actuator 71 and the stage 81 via the drive units 72 and 82 such that the optical path difference becomes a plurality of target values in sequence on the basis of the results of optical path difference detection by the displacement detecting unit 62. Particularly, the control unit 90 causes the moving operation by the stage 81 to be continuously or intermittently performed such that an amount of moving by the piezoelectric actuator 71 falls within a predetermined range within the operating range at each of the plurality of target values. Further, even at the time of moving operation by the stage 81, the control unit 90 performs feedback control of the moving operation by the piezoelectric actuator 71 such that the optical path difference becomes each target value on the basis of the results of optical path difference detection by the displacement detecting unit 62.

(Optical path difference adjusting operation by the piezoelectric actuator 71 and the stage 81)

Figure 4:
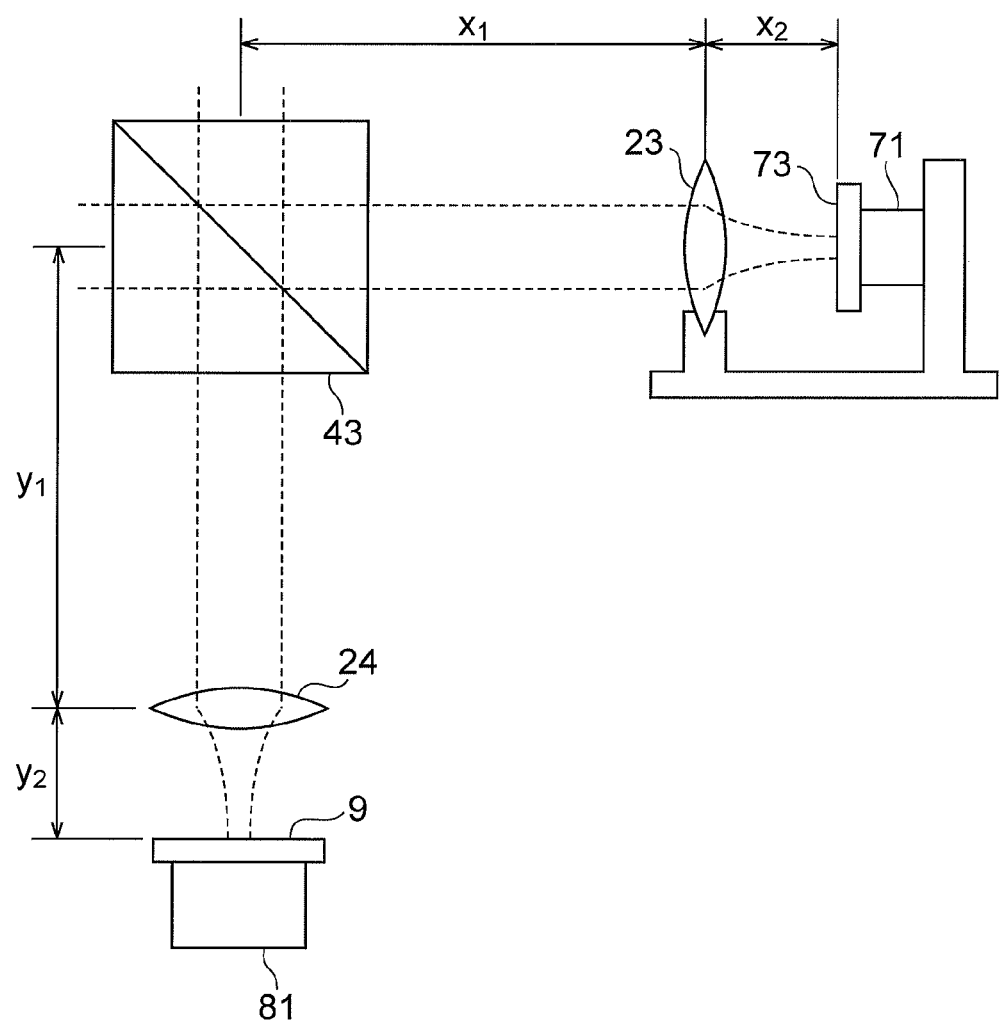
FIG. 4 is a diagram for explaining optical path difference adjusting operations by a piezoelectric actuator 71 and a stage 81.

FIG. 4 is a diagram for explaining an optical path difference adjusting operation by the piezoelectric actuator 71 and the stage 81. In this drawing, the optical system between the half mirror 43 and the mirror 73 is shown, the optical system between the half mirror 43 and the observation object 9 is shown, and the piezoelectric actuator 71 and the stage 81 for adjusting an optical path difference are shown. Here, an interval between the half mirror 43 and the lens 23 is set to $x_1$, and an interval between the lens 23 and the mirror 73 is set to $x_2$. Further, an interval between the half mirror 43 and the lens 24 is set to $y_1$, and an interval between the lens 24 and the observation object 9 is set to $y_2$. In addition, in the case where the observation object 9 has the configuration shown in FIG. 3, $y_2$ is considered as an interval from the lens 24 to a certain sliced plane of the observation object 9. The interval $x_2$ is adjusted by a moving operation by the piezoelectric actuator 71. The interval $y_2$ is adjusted by a moving operation by the stage 81. It is possible to adjust the optical path difference $\Delta L$ by varying an interval $(x_1+x_2)$ or an interval $(y_1+y_2)$ by the piezoelectric actuator 71 or the stage 81.

On the condition that only the interval $y_2$ is adjusted by a moving operation by the stage 81, because the operating range of the stage 81 is relatively broad, it is possible to adjust the optical path difference in a broad dynamic range. However, in this case, because the positional accuracy of the stage 81 is relatively low, it is impossible to adjust the optical path difference with a high degree of accuracy. Accordingly, it is impossible to measure the shape and the like of the observation object 9 with a high degree of accuracy.

On the other hand, on the condition that only the interval $x_2$ is adjusted by a moving operation by the piezoelectric actuator 71, because the positional accuracy of the piezoelectric actuator 71 is relatively high, it is possible to adjust the optical path difference with a high degree of accuracy. However, in this case, because the operating range of the piezoelectric actuator 71 is relatively narrow, it is impossible to adjust the optical path difference in a broad dynamic range. Accordingly, it is impossible to measure the shape and the like of the observation object 9 in a broad dynamic range.

Further, when a moving operation is performed over a broad range even if it is within the operating range of the piezoelectric actuator 71, a difference between the focal distance of the lens 23 and the interval $x_2$ is increased in some cases. In that case, an imaging surface of the interference light by the imaging optical system and an image pickup surface of the image pickup unit 51 are greatly shifted from each other, which makes the interference light figure taken as an image by the image pickup unit 51 unclear. Therefore, it is impossible to measure the shape and the like of the observation object 9 with a high degree of accuracy.

Then, in the present embodiment, in order to measure the surface or the inside of an observation object in a broad dynamic range with a high degree of accuracy, the control unit 90 causes the moving operation by the stage 81 to be continuously or intermittently performed such that an amount of moving by the piezoelectric actuator 71 falls within a predetermined range within the operating range at each of the plurality of target values. Further, even at the time of moving operation by the stage 81, the control unit 90 performs feedback control of the moving operation by the piezoelectric actuator 71 such that the optical path difference becomes each target value on the basis of the results of optical path difference detection by the displacement detecting unit 62. Hereinafter, two respective preferred operation modes of the piezoelectric actuator 71 and the stage 81 will be described.

(First mode of optical path difference adjusting operation)

Figure 5:
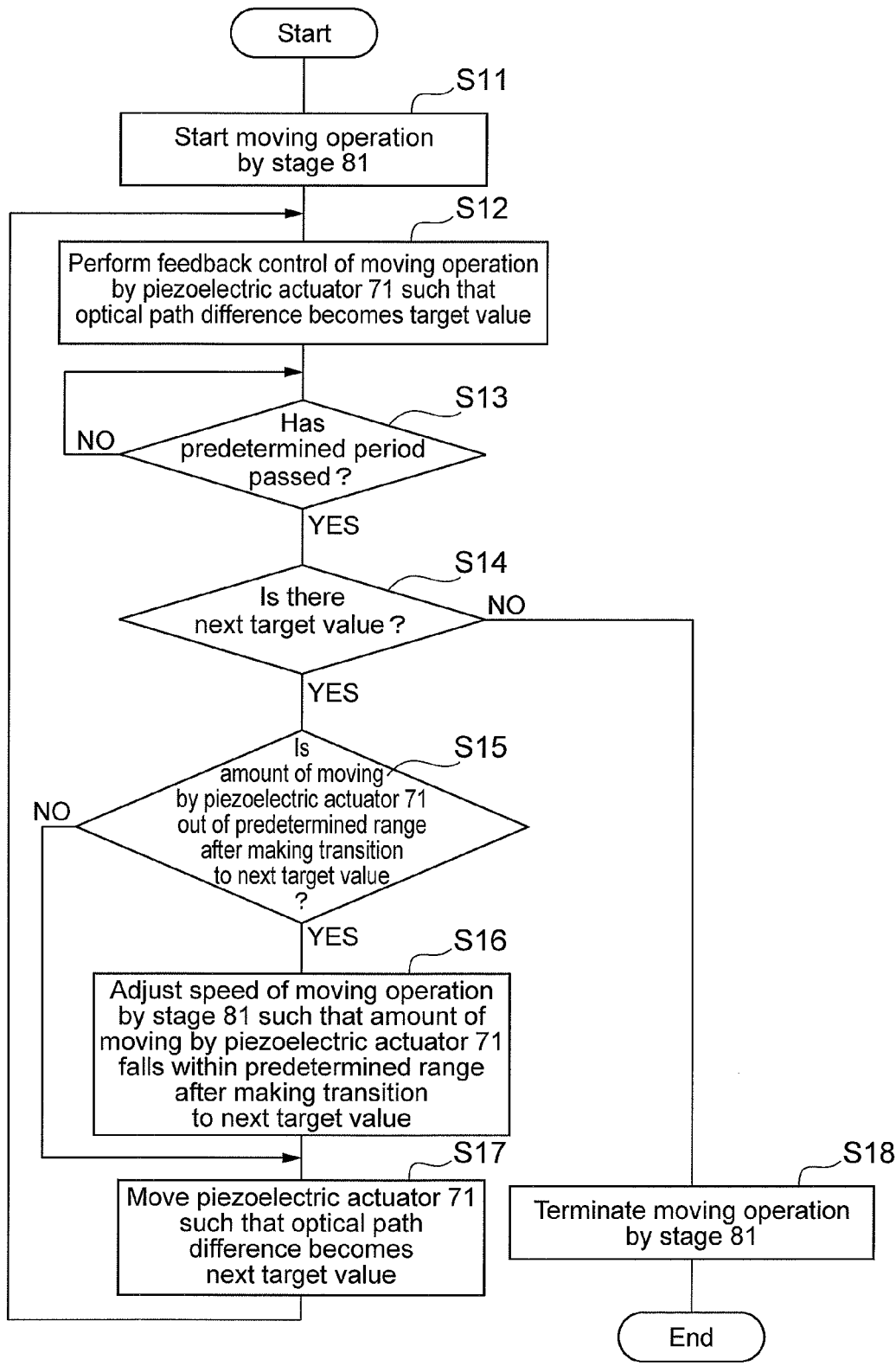
FIG. 5 is a flowchart for explaining a first operation mode of the observation device 1 according to the present embodiment.
Figure 6:
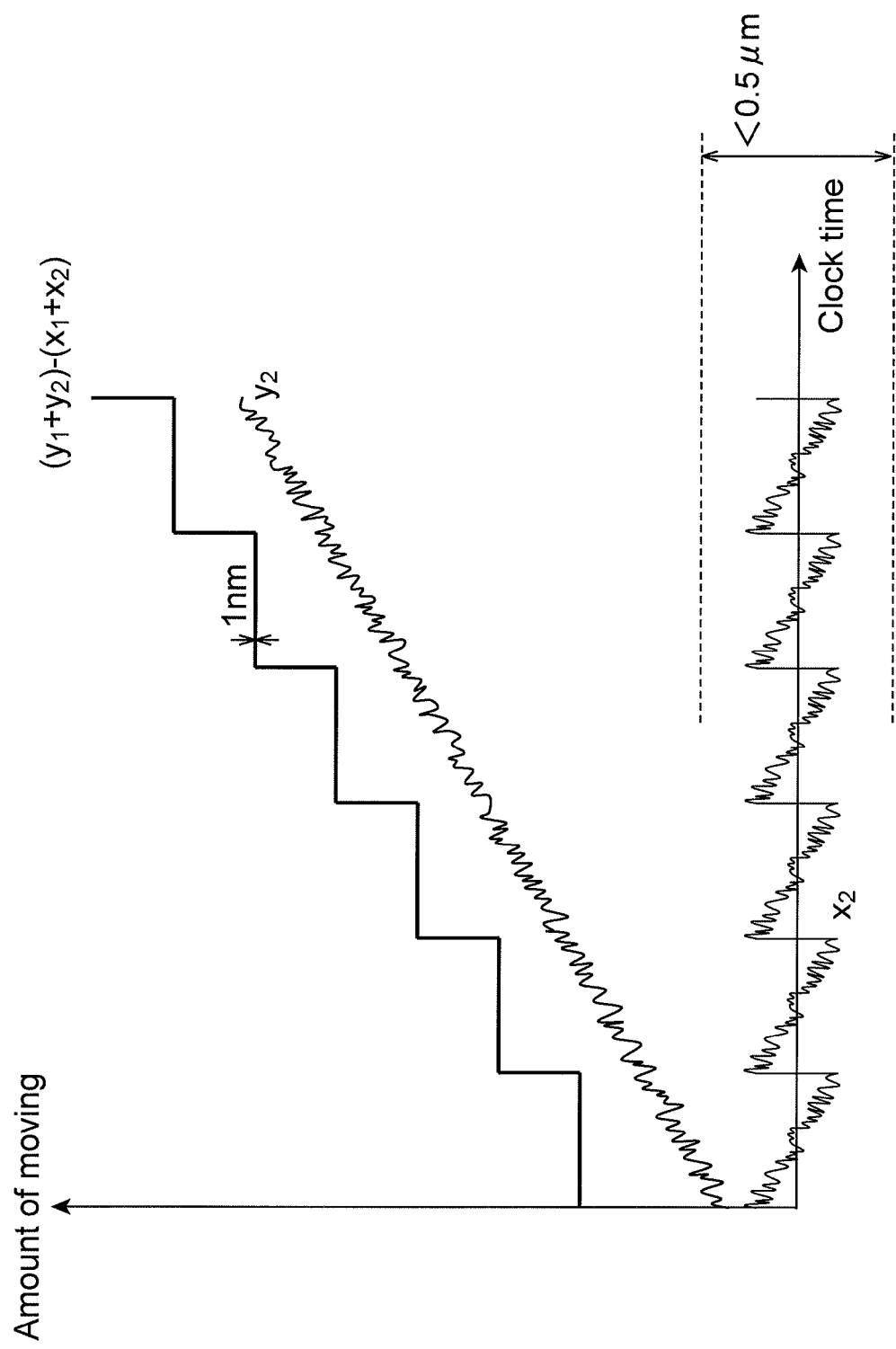
FIG. 6 is a chart showing the respective temporal changes in an interval $x_2$, an interval $y_2$, and an optical path difference $\{(y_l+y_2)-(x_l+x_2)\}$ in the first operation mode of the observation device 1 according to the present embodiment.

FIG. 5 is a flowchart for explaining a first operation mode of the observation device 1 according to the present embodiment. Further, FIG. 6 is a chart showing the respective temporal changes in an interval $x_2$, an interval $y_2$, and an optical path difference $\{(y_1+y_2)-(x_1+x_2)\}$ in the first operation mode. In this first operation mode, the control unit 90 causes the moving operation by the stage 81 to be continuously performed via the drive unit 82.

First, in step S11, the control unit 90 starts the moving operation by the stage 81 via the drive unit 82. It is assumed that the optical path difference is caused to make a transition from a certain target value to the next target value at a constant time interval $\Delta t$, and when an amount of change in the interval $y_2$ at the time of the transition is $\Delta y$, the moving speed of the stage 81 is set to "$\Delta y/\Delta t$." Thereby, the interval $y_2$ between the lens 24 and the observation object 9 is changed substantially linearly as time passes. However, because the positional accuracy of the stage 81 is relatively low, the temporal variation in the interval $y_2$ is relatively great.

Then, in step S12, the control unit 90 performs feedback control of the moving operation by the piezoelectric actuator 71 via the drive unit 72 such that the optical path difference becomes the target value. At this time, the interval $x_2$ is adjusted by the piezoelectric actuator 71 to set the optical path difference $\{(y_1+y_2)-(x_1+x_2)\}$ with a high degree of accuracy.

In step S13, the control unit 90 judges whether or not the constant time $\Delta t$ has passed after the optical path difference is set to a certain target value, and when the constant time $\Delta t$ has passed, the control unit 90 proceeds to processing in step S14. In step S14, the control unit 90 judges whether or not there is a next target value, and when there is a next target value, the control unit 90 proceeds to processing in step S15, and when there is no next target value, the control unit 90 proceeds to processing in step S18.

In step S15, the control unit 90 judges whether or not the amount of moving $x_2$ by the piezoelectric actuator 71 is out of the predetermined range at the target value after the transition before the optical path difference is caused to make a transition to the next target value. Then, in the case where the control unit 90 has judged that the amount of moving $x_2$ is out of the predetermined range, the control unit 90 proceeds to processing in step S17 via step S16, and in the case where the control unit 90 has judged that the amount of moving $x_2$ is within the predetermined range, the control unit 90 immediately proceeds to processing in step S17. In step S16, the control unit 90 adjusts the speed of the moving operation by the stage 81 such that the amount of moving $x_2$ by the piezoelectric actuator 71 is brought to be within the predetermined range after making a transition to the next target value.

In step S17, the control unit 90 sets the optical path difference to the next target value, and causes the piezoelectric actuator 71 to move by $\Delta x$ in a stepwise fashion via the drive unit 72. Thereafter, the control unit 90 returns to the processing in step S12, and the control unit 90 performs feedback control of the moving operation by the piezoelectric actuator 71 via the drive unit 72 such that the optical path difference becomes a new target value. In step S18, the control unit 90 terminates the moving operation by the stage 81 via the drive unit 82.

In this way, in the first operation mode, the control unit 90 causes the moving operation by the stage 81 to be continuously performed, and causes the moving operation by the piezoelectric actuator 71 to be performed in a stepwise fashion at the time of making the transition of the optical path difference from a certain target value to the next target value, and performs feedback control of the moving operation by the piezoelectric actuator 71 such that the optical path difference becomes the target value during the time that the optical path difference is set to a certain target value. In this way, the control unit 90 controls the respective moving operations by the piezoelectric actuator 71 and the stage 81, thereby it is possible to take advantage of both the broad dynamic range of the moving operation by the stage 81 and the high positional accuracy of the moving operation by the piezoelectric actuator 71, and it is possible to measure the surface shape and the like of the observation object 9 in the broad dynamic range with a high degree of accuracy.

Further, in the first operation mode, in the case where the amount of moving by the piezoelectric actuator 71 is out of the predetermined range at the target value after the transition, the control unit 90 adjusts the speed of the moving operation by the stage 81 such that the amount of moving is brought to be within the predetermined range (steps S15 and S16) before the optical path difference is caused to make a transition from a certain target value to the next target value. In this way, because the control unit 90 adjusts the moving speed by the stage 81, even in the case where the accuracy in the moving speed of the stage 81 or the temporal interval Δt of target value variations is insufficient, it is possible to keep the amount of moving by the piezoelectric actuator 71 within the predetermined range, which makes it possible to maintain measurement of the surface shape and the like of the observation object 9 with a high degree of accuracy. In addition, when a moving distance when moving the stage 81 at a constant speed of "Δy/Δt" during a time of N·Δt has a sufficient accuracy (for example, its error is ±1 μm or less), steps S15 and S16 are not needed, and the control unit 90 may immediately proceed to processing in step S17 after step S14.

(Second mode of optical path difference adjusting operation)

Figure 7:
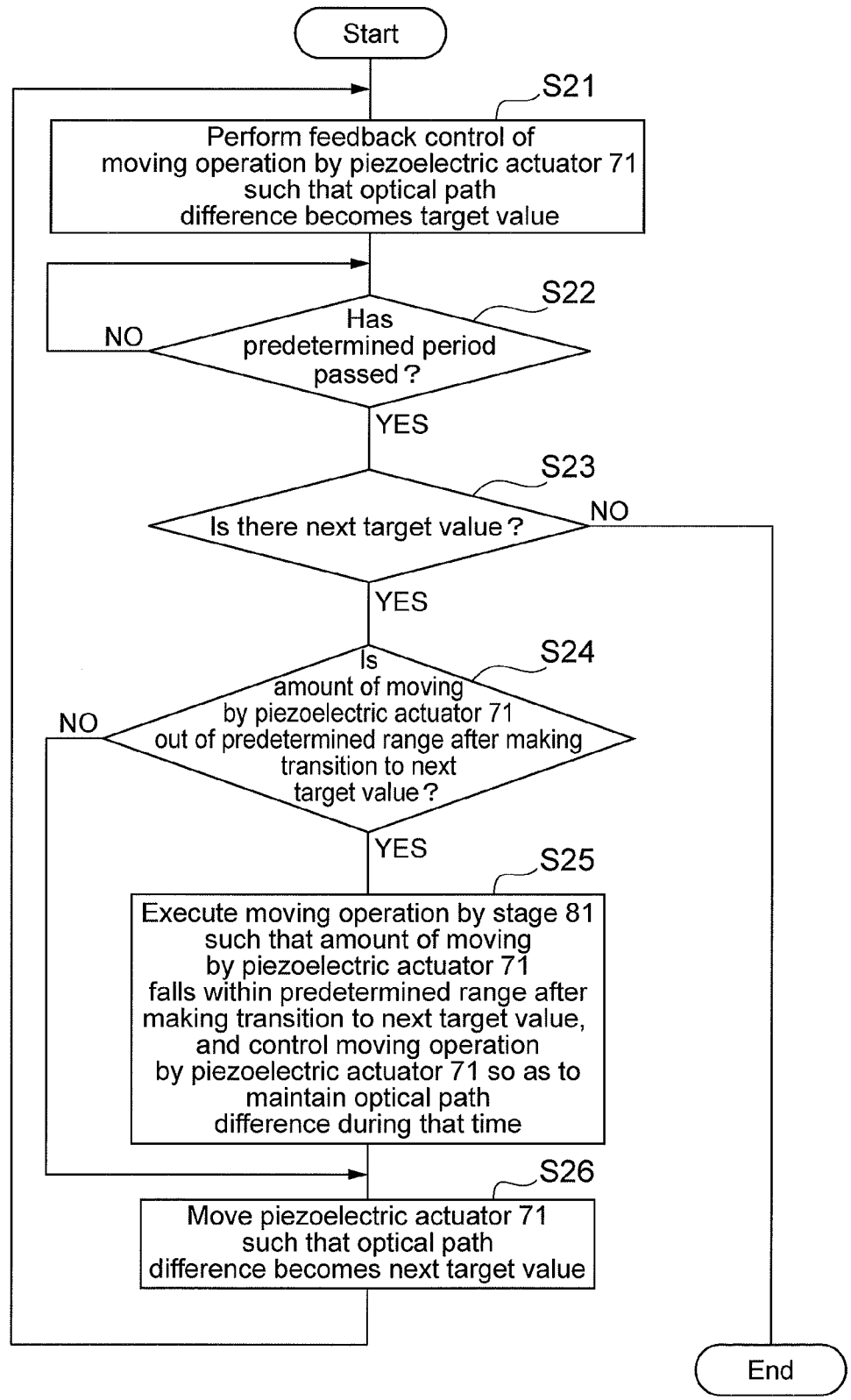
FIG. 7 is a flowchart for explaining a second operation mode of the observation device 1 according to the present embodiment.
Figure 8:
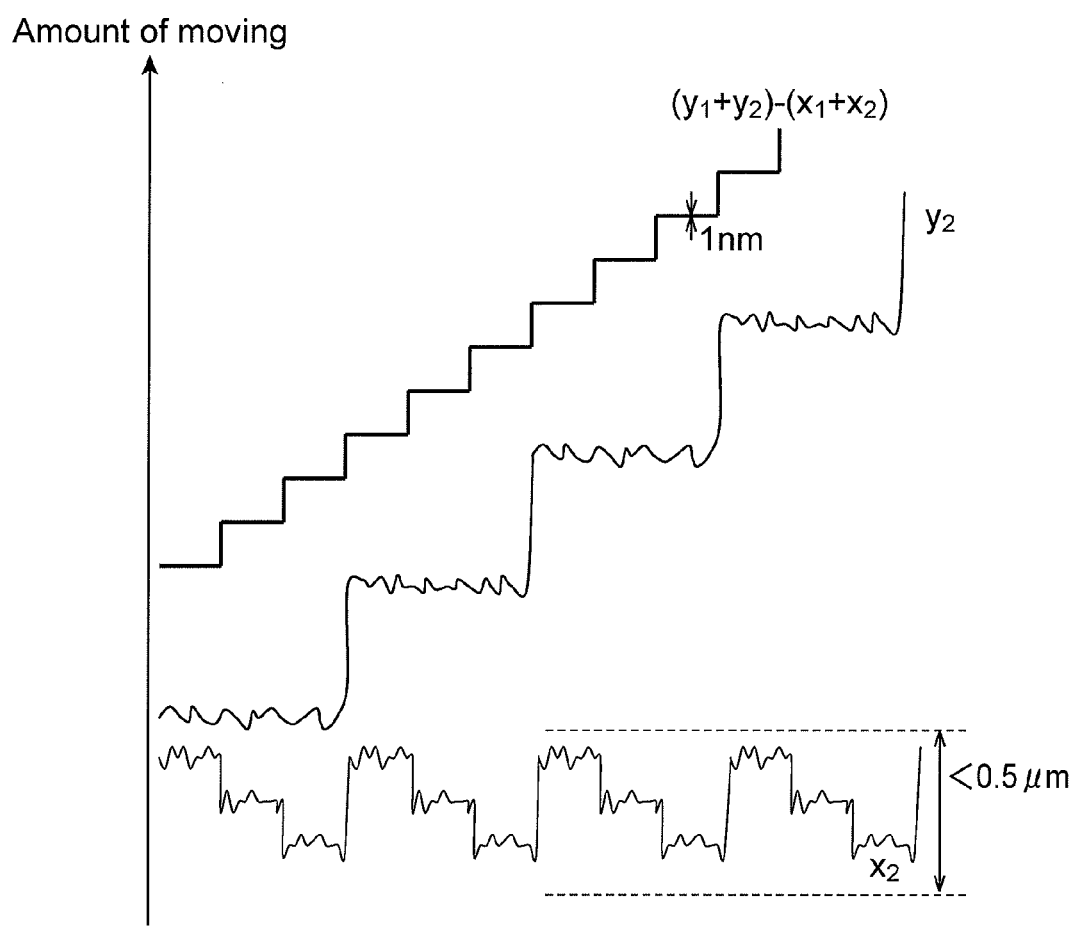
FIG. 8 is a chart showing the respective temporal changes in an interval $x_2$, an interval $y_2$, and an optical path difference $\{(y_l+y_2)-(x_l+x_2)\}$ in the second operation mode of the observation device 1 according to the present embodiment.

FIG. 7 is a flowchart for explaining a second operation mode of the observation device 1 according to the present embodiment. Further, FIG. 8 is a chart showing the respective temporal changes in an interval $x_2$, an interval $y_2$, and an optical path difference $\{(y_1+y_2)-(x_1+x_2)\}$ in the second operation mode. In this second operation mode, the control unit 90 causes the moving operation by the stage 81 to be performed intermittently via the drive unit 82.

In step S21, the control unit 90 performs feedback control of the moving operation by the piezoelectric actuator 71 via the drive unit 72 such that the optical path difference becomes the target value. At this time, although the stage 81 does not move, the positional accuracy of the stage 81 is relatively low, and therefore, the temporal variation in the interval $y_2$ is relatively great. However, the interval $x_2$ is adjusted by the piezoelectric actuator 71 to set the optical path difference $\{(y_1+y_2)-(x_1+x_2)\}$ with a high degree of accuracy.

In step S22, the control unit 90 judges whether or not the constant time Δt has passed after the optical path difference is set to a certain target value, and when the constant time Δt has passed, the control unit 90 proceeds to processing in step S23. In step S23, the control unit 90 judges whether or not there is a next target value, and when there is a next target value, the control unit 90 proceeds to processing in step S24, and when there is no next target value, the control unit 90 terminates the processing.

In step S24, the control unit 90 judges whether or not the amount of moving $x_2$ by the piezoelectric actuator 71 is out of the predetermined range at the target value after the transition before the optical path difference is caused to make a transition to the next target value. Then, when the control unit 90 has judged that the amount of moving $x_2$ is out of the predetermined range, the control unit 90 proceeds to processing in step S26 via step S25, and when the control unit 90 has judged that the amount of moving $x_2$ is within the predetermined range, the control unit 90 immediately proceeds to processing in step S26.

In step S25, the control unit 90 stops the stage 81 after moving the stage 81 such that the amount of moving $x_2$ by the piezoelectric actuator 71 is brought to be within the predetermined range after making a transition to the next target value, and during the time that the stage 81 is moving, the control unit 90 controls the moving operation by the piezoelectric actuator 71 such that the optical path difference at that time becomes each target value. In addition, at the time of moving the stage 81 at this time, in the case where the amount of moving $x_2$ by the piezoelectric actuator 71 is over the upper limit of the predetermined range at the next target value, the amount of moving $x_2$ by the piezoelectric actuator 71 is brought to be approximate to the lower limit of the predetermined range. In contrast thereto, in the case where the amount of moving $x_2$ by the piezoelectric actuator 71 is over the lower limit of the predetermined range at the next target value, the amount of moving $x_2$ by the piezoelectric actuator 71 is brought to be approximate to the upper limit of the predetermined range.

In step S26, the control unit 90 sets the optical path difference to the next target value, and causes the piezoelectric actuator 71 to move by Δx in a stepwise fashion via the drive unit 72. Thereafter, the control unit 90 returns to the processing in step S21, and the control unit 90 performs feedback control of the moving operation by the piezoelectric actuator 71 via the drive unit 72 such that the optical path difference becomes a new target value.

In this way, in the second operation mode, the control unit 90 performs feedback control of the moving operation by the piezoelectric actuator 71 such that the optical path difference becomes each target value. In this way, the control unit 90 controls the respective moving operations by the piezoelectric actuator 71 and the stage 81, thereby it is possible to take advantage of both the broad dynamic range of the moving operation by the stage 81 and the high positional accuracy of the moving operation by the piezoelectric actuator 71, and it is possible to measure the surface shape and the like of the observation object 9 in the broad dynamic range with a high degree of accuracy. In addition, in the case where the positional accuracy of the stage 81 is low, the second operation mode is more effective than the first operation mode.

(Details of analysis by the analyzing unit 52 and image display by the display unit 53: Part 1)

Next, observation of the observation object 9 (particularly, analysis by the analyzing unit 52 and image display by the display unit 53) in the observation device 1 according to the present embodiment and an observation method according to the present embodiment will be described in more detail.

A second reflected light E (x, y) reflected by the surface or the inside of the observation object 9 to reach the image pickup surface of the image pickup unit 51 contains an intensity component R (x, y) and a phase component φ (x, y), and is expressed by the following expression (1). An interference figure taken as an image by the image pickup unit 51 is reflected by information on the sliced plane of the observation object 9 by which the second reflected light is generated (and in a range of approximately the coherence length of the light $\lambda_1$ centering on the sliced plane) such that the respective optical path lengths of the first reflected light and the second reflected light are matched to each other at a level of a coherence length of the light $\lambda_1$. In addition, x and y express the coordinate values of the two orthogonal axes in the sliced plane.

[Expression 1]

$$E(x, y) = R(x, y) \cdot \exp(j \cdot \phi(x, y)) \tag{1}$$

The intensity component R (x, y) of the second reflected light E (x, y) expresses the reflectance of the light $\lambda 1$ in the sliced plane, that is, the information on the presence or absence of reflectors. Further, the phase component $\phi$ (x, y) of the second reflected light E (x, y) expresses information on a position in a z direction of the reflectors (a direction parallel to the optical axis) in the sliced plane. For example, in the case where the reflectors (for example, a cellular membrane, a membrane of a nuclear body, a lysosomal membrane, and the like) present in the sliced plane of the observation object 9 move by $\Delta z$ in the z direction, the phase component $\phi$ (x, y) of the second reflected light E (x, y) reaching the image pickup surface of the image pickup unit 51 is changed by $4\pi n_1 \Delta z / \lambda_1$. Here, $n_1$ is a refractive index of the observation object 9. That is, an amount of change in the phase component $\phi$ (x, y) shows an amount of positional changes in the z direction of the reflectors in the sliced plane.

Such an intensity component R (x, y) and a phase component $\phi$ (x, y) of the second reflected light E (x, y) are determined with a phase shift technique. In a phase shift technique, the piezoelectric actuator 71 is driven under the control by the control unit 90 and the drive unit 72 to shift an optical path difference $\Delta L \lambda_1/4$ by $\lambda_1/4$, and four interference light figures $I_1$ (x, y), $I_2$ (x, y), $I_3$ (x, y), and $I_4$ (x, y) are taken as images in sequence by the image pickup unit 51. Here, $\lambda_1$ is a central wavelength of a low coherent light output from the light source 11. Sine components A (x, y) and cosine components B (x, y) of the interference light figures are obtained according to the following expression (2) from these four interference light figures.

[Expression 2]

$$A(x, y) = I_1(x, y) - I_3(x, y) \tag{2a}$$

$$B(x, y) = I_2(x, y) - I_4(x, y) \tag{2b}$$

Then, an intensity component R (x, y) and a phase component $\phi$ (x, y) of the second reflected light E (x, y) are obtained according to the following expression (3) from these sine components A (x, y) and cosine components B (x, y) of the interference light figures. In addition, the sine components A (x, y) and the cosine components B (x, y) are expressed as the following expression (4) by using the intensity component R (x, y) and the phase component $\phi$ (x, y) of the second reflected light E (x, y). Further, a complex amplitude C (x, y) of an interference light figure is expressed by the following expression (5) or (6). The analyzing unit 52 determines such a complex amplitude C (x, y) of an interference light figure.

[Expression 3]

$$R(x,y) = \sqrt{A(x,y)^2 + B(x,y)^2} \tag{3a}$$

$$\phi(x, y) = \tan^{-1}(A(x, y)/B(x, y)) \tag{3b}$$

[Expression 4]

$$A(x, y) = R(x, y) \cdot \cos \phi(x, y) \tag{4a}$$

$$B(x, y) = R(x, y) \cdot \sin \phi(x, y) \tag{4b}$$

[Expression 5]

$$C(x, y) = A(x, y) + j \cdot B(x, y) \tag{5}$$

[Expression 6]

$$C(x, y) = R(x, y) \cdot (\cos \phi(x, y) + j \cdot \sin \phi(x, y)) \tag{6}$$

Figure 9:
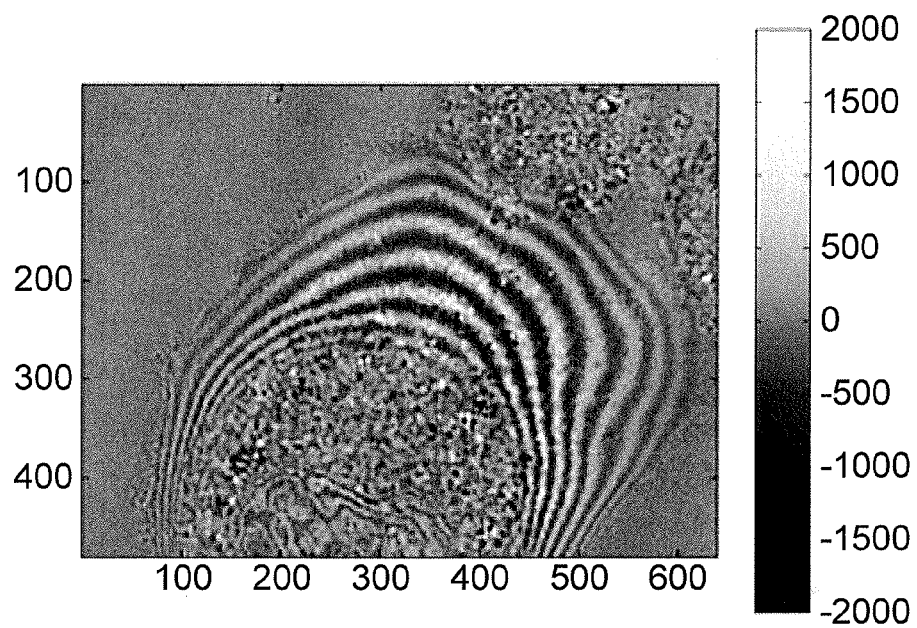
FIG. 9 is a chart showing a sine component A (x, y) of an interference light figure.
Figure 10:
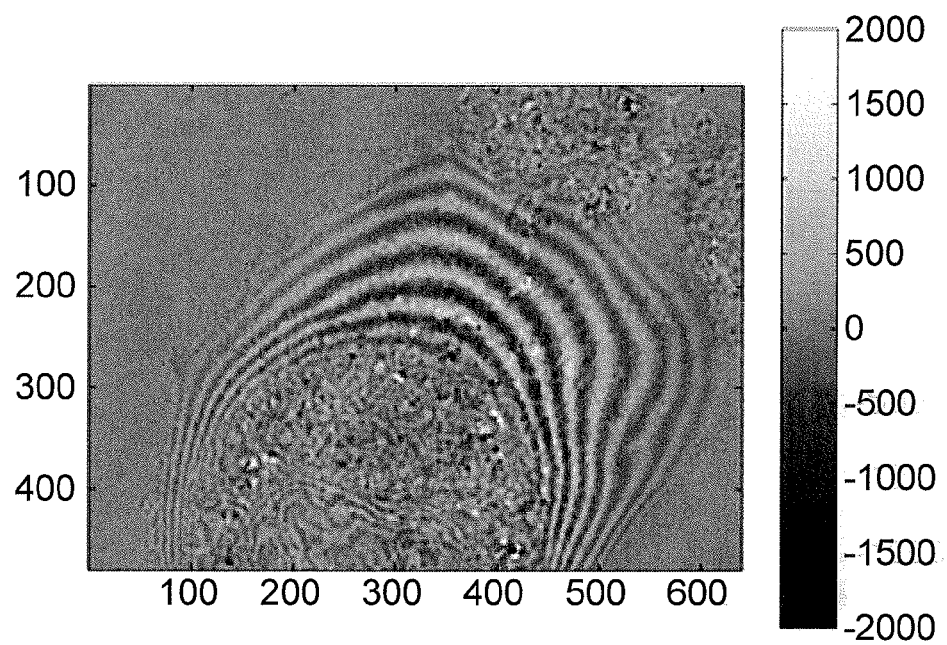
FIG. 10 is a chart showing a cosine component B (x, y) of an interference light figure.
Figure 11:
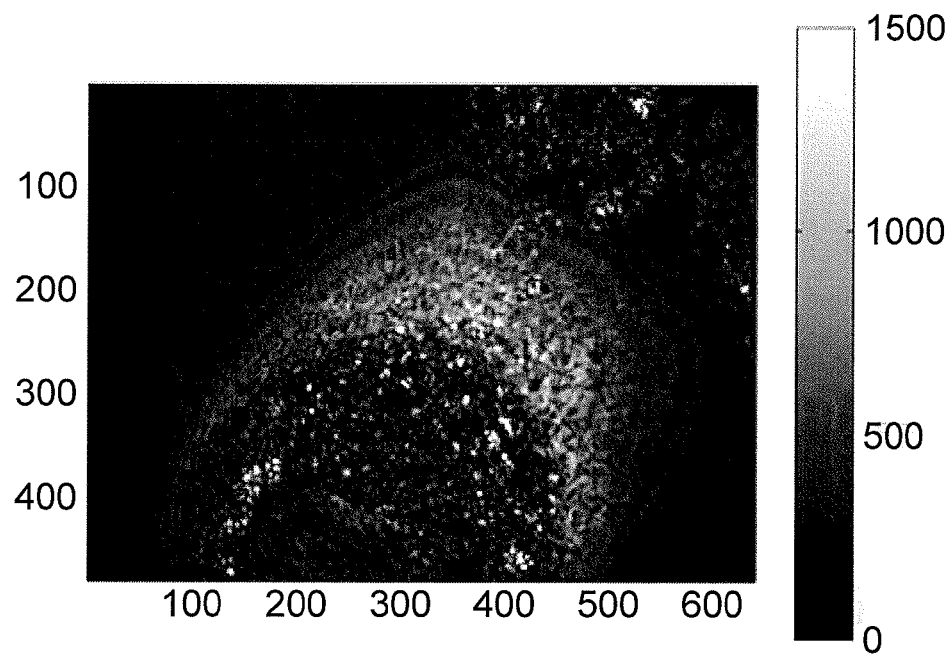
FIG. 11 is a chart showing an intensity component R (x, y) of an interference light figure.

FIG. 9 is a chart showing a sine component A (x, y) of an interference light figure. FIG. 10 is a chart showing a cosine component B (x, y) of an interference light figure. FIG. 11 is a chart showing an intensity component R (x, y) of an interference light figure.

Figure 12:
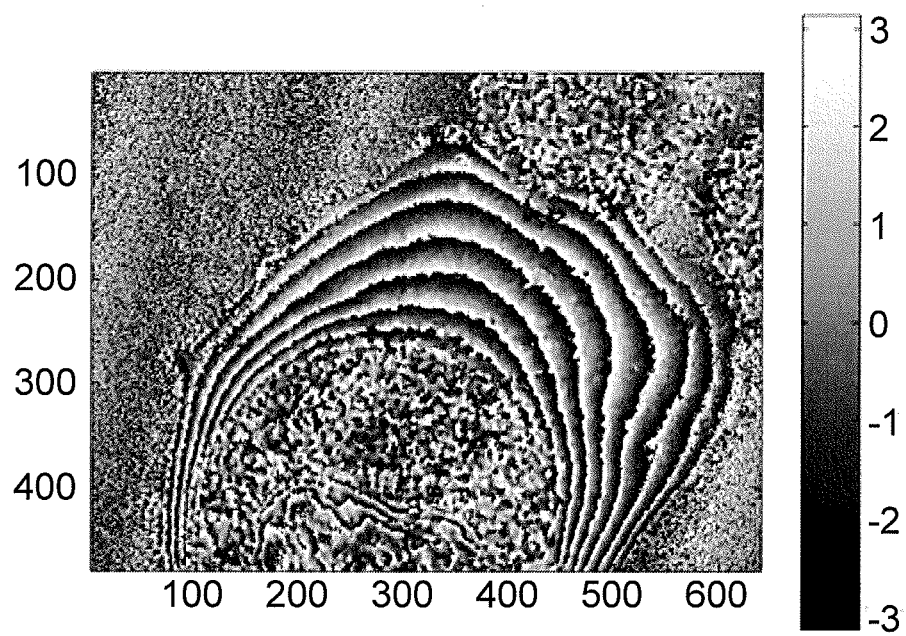
FIG. 12 is a chart showing a phase component φ (x, y) of an interference light figure.
Figure 13:
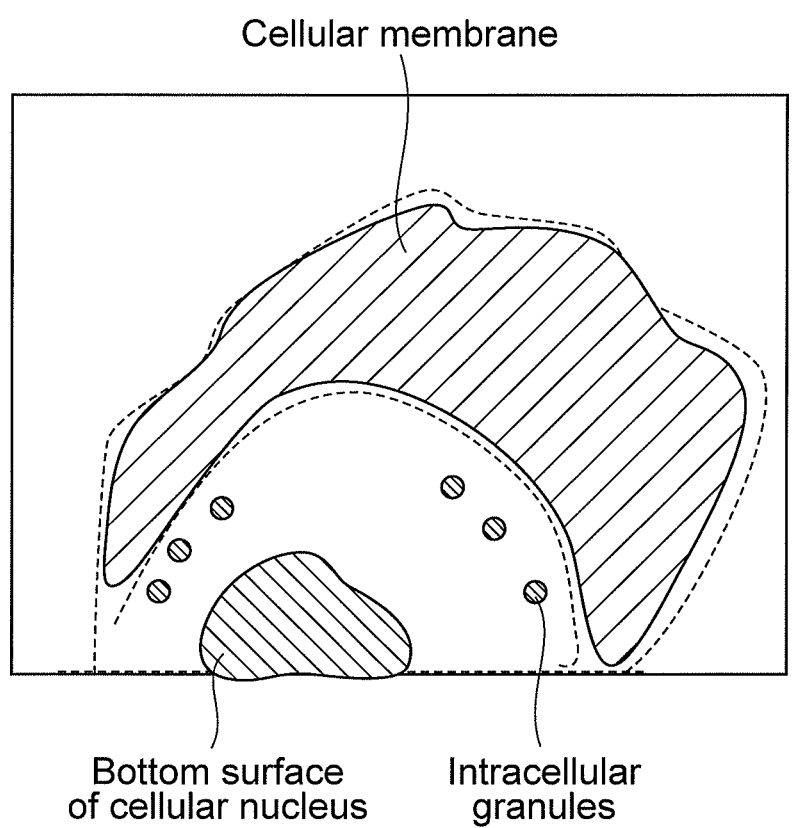
FIG. 13 is a diagram showing the relationship between organs and reflectors in a HeLa cell.

FIG. 12 is a chart showing a phase component $\phi$ (x, y) of an interference light figure. These are all on the basis of the four interference light figures $I_1$ (x, y), $I_2$ (x, y), $I_3$ (x, y), and $I_4$ (x, y) determined with respect to a HeLa cell serving as the observation object 9 with the phase shift technique. When looking at the intensity component R (x, y) of the interference light figure shown in FIG. 11, it can be seen that there are various reflectors near the cellular membrane and in the cell. The relationship between these reflectors and the organs of the HeLa cell may be as shown in FIG. 13.

Although there are various improved algorithms for a phase shift technique, any algorithm may be used. For example, in accordance with algorithms known as the Schwider-Hariharan Algorithm, sine components A (x, y) and cosine components B (x, y) of the interference light figures may be determined according to the following expression (7) on the basis of five interference light figures. Moreover, an intensity component R (x, y) and a phase component $\phi$ (x, y) of the second reflected light E (x, y) may be determined on the basis of these components.

[Expression 7]

$$A(x, y) = -2(I_2(x, y) - I_4(x, y)) \tag{7a}$$

$$B(x, y) = I_1(x, y) - 2I_3(x, y) + I_5(x, y) \tag{7b}$$

In the present embodiment, any algorithm for a phase shift technique may be used. However, as compared with the fundamental algorithm for the phase shift technique according to the above-described expression (2), the improved algorithm for the phase shift technique according to the above-described expression (7) has advantages of robustness for an error in a phase shift amount and the like, and is used suitably for a case where a coherence length of the light $\lambda_1$ is relatively short as in the present embodiment.

Figure 14:
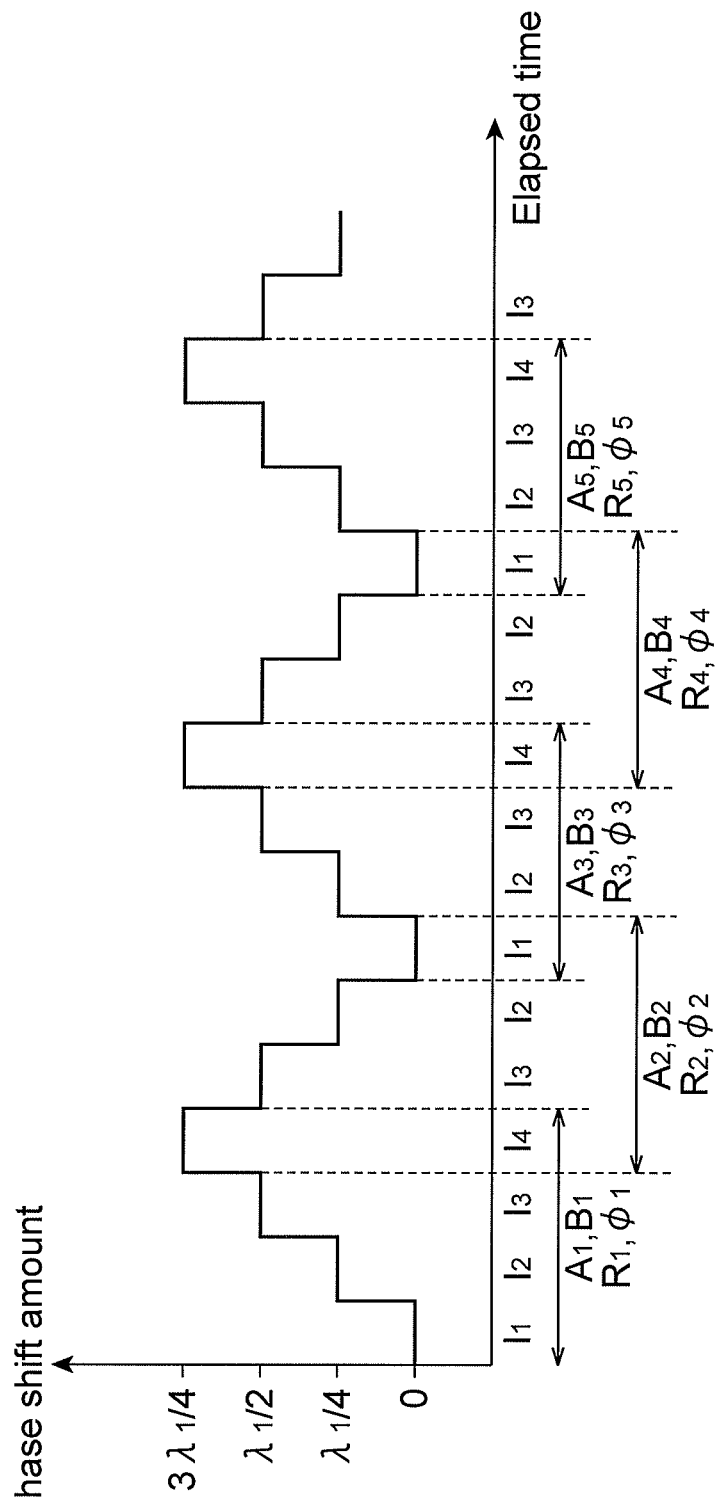
FIG. 14 is a graph showing the situation of a temporal change in a phase shift amount in the case where plural sets of sine components A (x, y) and cosine components B (x, y) are acquired in time-series.

FIG. 14 is a graph showing the situation of a temporal change in a phase shift amount in the case where plural sets of sine components A (x, y) and cosine components B (x, y) are acquired in time-series. As shown in this graph, the piezoelectric actuator 71 is driven under the control by the control unit 90 and the drive unit 72 to shift an optical path difference $\Delta L$ 80 $_1/4$ by $\lambda_1/4$ every constant time, and the phase shift amount is repeatedly increased and decreased between 0 to $3\lambda_1/4$. Thereby, interference light figures $I_1, I_2, I_3, I_4, I_3, I_2, I_1, I_2, I_3, I_4,$ and ... are obtained in sequence. Then, by using the first interference light FIG. $I_1$ to the fourth interference light figure $I_4$, the first $A_1, B_1, R_1,$ and $\phi_1$ are obtained. Then, by using the fourth interference light figure $I_4$ to the seventh interference light figure $I_1$, the second $A_2, B_2, R_2,$ and $\phi_2$ are obtained. Moreover, by using the seventh interference light figure $I_7$ to the tenth interference light figure $I_4$, the third $A_3, B_3, R_3,$ and $\phi_3$ are obtained.

In this way, the sine components $A_n$ and the cosine components $B_n$ of the interference light figures, and the intensity components $R_n$ and the phase components $\phi_n$ of the second reflected light are obtained in sequence at constant time intervals. Hereinafter, these are inscribed as sine components A (x, y, n), cosine components B (x, y, n), intensity components R (x, y, n), and phase components $\phi$ (x, y, n) in some cases. Here, n in the inscriptions of the respective components denotes that the component is obtained as the n-th one, and corresponds to a temporal variable.

Figure 15:
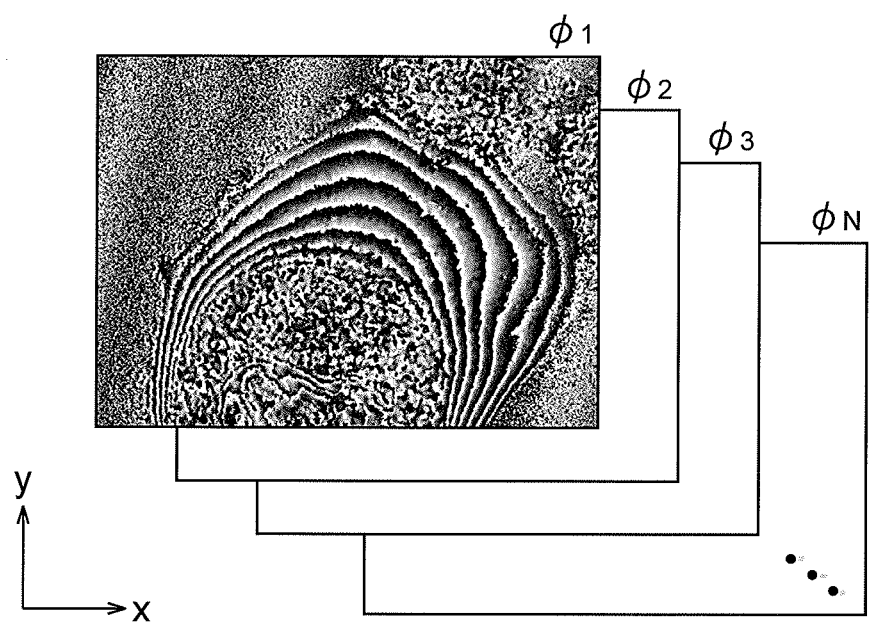
FIG. 15 is a graph showing the situation of acquisition of plural pieces of phase components φ (x, y, n).

As described above, a phase component $\phi$ (x, y, n) expresses the information on a position in the z direction (direction parallel to the optical axis) of reflectors in the sliced plane when an optical path length from the half mirror 43 to the mirror 73 and an optical path length from the half mirror 43 to a certain sliced plane of the observation object 9 are substantially equal to each other. Further, an amount of change in the phase component $\phi$ (x, y, n) shows an amount of positional changes in the z direction of the reflectors in the sliced plane. Then, as shown in FIG. 15, when plural pieces of phase components $\phi$ (x, y, n) are obtained at constant time intervals by the analyzing unit 52, by displaying images of these in time-series (moving picture display) by the display unit 53, it is possible to observe the situation of a positional change in the z direction of a reflector in the sliced plane of the observation object 9.

Figure 16:
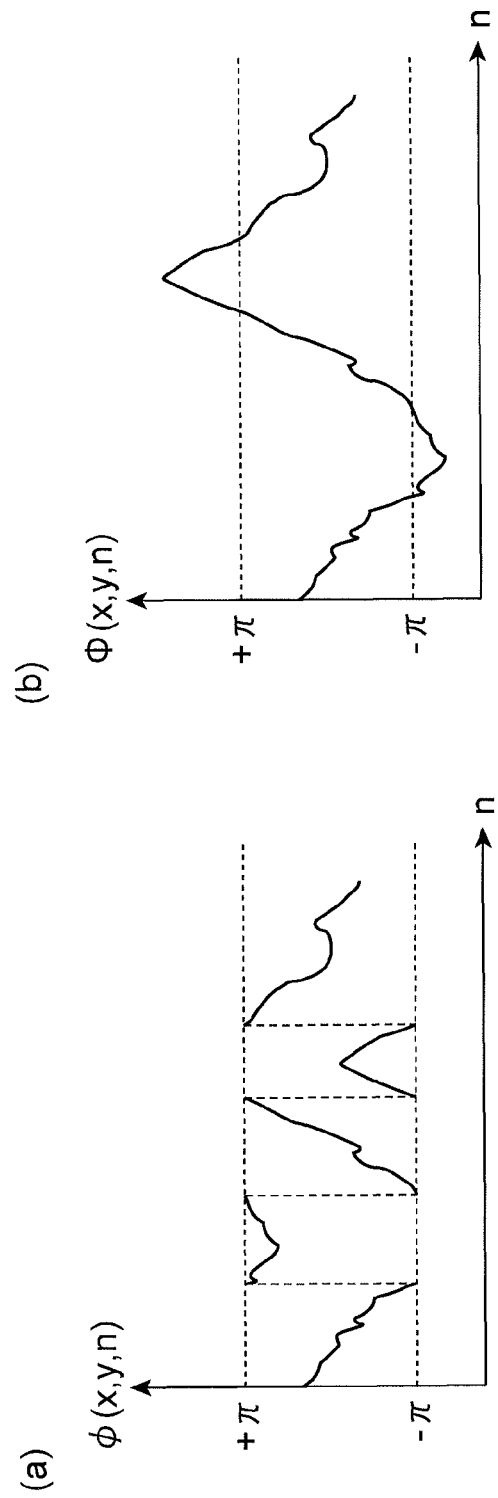
FIGS. 16 are graphs for explaining phase unwrapping.

Observation of the situation of a positional change in the z direction of a reflector in the sliced plane of the observation object 9 is possible by a mathematical treatment technique as follows on the basis of the plural pieces of phase components $\phi$ (x, y, n) obtained at constant time intervals. A phase component $\phi$ (x, y, n) usually having only values within a range of $2\pi$ with respect to the respective positions (x, y) is unsuitable as is for a quantitative evaluation. Therefore, first, as shown in FIG. 16, processing for connecting places whose phases are discontinuous when viewed in time-series (that is, phase unwrapping) is performed.

A phase component before phase unwrapping is expressed in lower-case $\phi$ (x, y, n), and a phase component after phase unwrapping is expressed in uppercase $\Phi$ (x, y, n). FIG. 16A is a graph showing the situation of a temporal change in a phase component $\phi$ (x, y, n) before phase unwrapping. FIG. 16B is a graph showing the situation of a temporal change in a phase component $\Phi$ (x, y, n) after phase unwrapping. Hereinafter, it is assumed that N pieces of phase components $\Phi$ (x, y, 1) to $\Phi$ (x, y, N) after phase unwrapping are obtained in sequence at constant time intervals.

The situation of positional changes in the z direction of the reflectors in the sliced plane of the observation object 9 is analyzed with respect to the respective positions (x, y) by any one of the processings of the following expressions (8) to (11) on the basis of the N pieces of phase components $\Phi$ (x, y, 1) to $\Phi$ (x, y, N) after phase unwrapping by the analyzing unit 52.

The following expression (8) expresses a width (the maximum value to the minimum value) of a positional change in the z direction of the reflectors at the respective positions (x, y) during a time of acquiring the N pieces of phase components $\Phi$ (x, y, n).

[Expression 8]

$$P_{-p}(x, y) = \max(\Phi(x, y, n)|_{n=1-N}) - \min(\Phi(x, y, n)|_{n=1-N}) \quad (8)$$

The following expression (9) shows a standard deviation of a magnitude of a positional change in the z direction of the reflectors at the respective positions (x, y) during a time of acquiring the N pieces of phase components $\Phi$ (x, y, n).

[Expression 9]

$$Stdev(x, y) = \sqrt{\frac{1}{N-1} \sum_{n=1}^{N} (\Phi(x, y, n) - \overline{\Phi(x, y, n)})} \quad (9)$$

The following expressions (10) and (11) each shows a magnitude of a positional change in the z direction of the reflectors at the respective positions (x, y) per predetermined time ($\Delta n \cdot t_0$). $t_0$ shows a time interval of acquiring the respective phase components $\Phi$ (x, y, n).

[Expression 10]

$$Vibr(x, y) = \frac{1}{N - \Delta n} \sum_{n=\Delta n+1}^{N} |\Phi(x, y, n) - \Phi(x, y, n - \Delta n)| \quad (10)$$

[Expression 11]

$$Vibr'(x, y) = \sqrt{\frac{1}{N - \Delta n} \sum_{n=\Delta n+1}^{N} |\Phi(x, y, n) - \Phi(x, y, n - \Delta n)|^2} \quad (11)$$

Alternatively, Fourier transform of the N pieces of phase components $\Phi$ (x, y, 1) to $\Phi$ (x, y, N) after phase unwrapping may be performed with respect to the respective positions (x, y), and frequency analysis of a positional change in the z direction of the reflectors may be performed.

As described above, when the situation of the positional change in the z direction of a reflector in the sliced plane of the observation object 9 is obtained with respect to the respective positions (x, y) by the analyzing unit 52, the result thereof is displayed as an image by the display unit 53. In the display unit 53, the analysis result by the analyzing unit 52 is preferably displayed as an image in gray scale, false color, or the like. By displaying it in this way, it is easy to observe the situation of the positional change in the z direction of a reflector in the sliced plane of the observation object 9.

The advantageous point of these signal processing techniques is the point that it is possible to extract high motile membranes (reflectors) present in its horizontal cross section (sliced plane) without discriminating between a signal of a reflected light from the membrane of the surface of the cell serving as the observation object 9 and a signal of a reflected light from the membrane inside the cell. The motility of a membrane highly relates to the activity of a cell, and there are many advantages in cytoscreening practically in the point that it is possible to extract cells having high membrane motility to display those in two dimensions.

Observation of the situation of positional change in the z direction of a reflector in the sliced plane of the observation object 9 is possible by a mathematical treatment technique as well as following on the basis of plural pieces of complex amplitudes C (x, y, n) of an interference light figure acquired at constant time intervals. The complex amplitude C (x, y, n) obtained as the n-th one is expressed by the following expression (12) or (13). Then, the situation of the positional change in the z direction of a reflector in the sliced plane of the observation object 9 is analyzed with respect to the respective positions (x, y) by the following expression (14) on the basis of the N pieces of complex amplitude images C (x, y, 1) to C (x, y, N) by the analyzing unit 52.

[Expression 12]

$$C(x, y, n) = A(x, y, n) + j \cdot B(x, y, n) \quad (12)$$

[Expression 13]

$$C(x, y, n) = R(x, y, n) \cdot (\cos\phi(x, y, n) + i\sin\phi(x, y, n)) \quad (13)$$

[Expression 14]

$$\phi_{dev}(x, y) = \frac{\sqrt{\frac{1}{N - \Delta n} \sum_{n=1+\Delta n}^{N} |C(x, y, n) - C(x, y, n - \Delta n)|^2}}{\sqrt{\frac{1}{N - \Delta n} \sum_{n=1+\Delta n}^{N} |R(x, y, n)|^2}} \quad (14)$$

Figure 17:
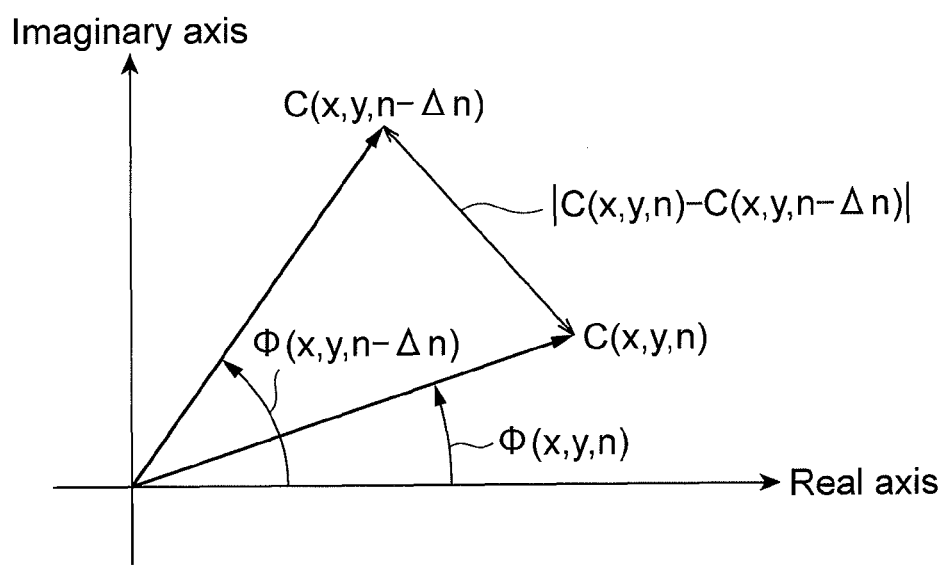
FIG. 17 is a graph showing a complex amplitude C (x, y, n) in a complex plane.

The factor $|C(x, y, n) - C(x, y, n-\Delta n)|$ in the numerator of the expression (14) is described by FIG. 17. FIG. 17 is a graph showing a complex amplitude C (x, y, n) in a complex plane. On the complex plane in the graph, the complex amplitude C (x, y, n) and the complex amplitude C (x, y, n–Δn) are respectively shown as end-points of the vectors with the origin serving as their start points. $|C(x, y, n) - C(x, y, n-\Delta n)|$ is the length of segment connecting the points expressing the respective complex amplitude C (x, y, n) and complex amplitude C (x, y, n–Δn) on the complex plane in the graph.

Here, it is assumed that, from the n-th complex amplitude to the (n–Δn)-th complex amplitude, an amount of change in the intensity component R (x, y, n) is negligibly small, and an amount of change in the phase component φ (x, y, n) is a slight amount. In this case, the approximate expression of the following expression (15) holds. That is, the factor $|C(x, y, n) - C(x, y, n-\Delta n)|$ in the numerator of the above-described expression (14) is that an amount of change in the phase components φ (x, y, n) per predetermined time (Δn·$t_0$) is multiplied by the intensity component R (x, y, n).

[Expression 15]

$$|C(x, y, n) - C(x, y, n-\Delta n)| \approx R(x, y, n) \cdot |\phi(x, y, n) - \phi(x, y, n-\Delta n)| \quad (15)$$

On the other hand, the denominator of the above-described expression (14) shows an average value of the intensity components R (x, y, n). Accordingly, an index $\phi_{dev}$ (x, y) of the above-described expression (14) shows an average value of the amounts of changes in the phase component φ (x, y, n) per predetermined time (Δn·$t_0$). That is, it is indicated that a high motile reflector is present at a position at which the value of an index $\phi_{dev}$ (x, y) is high. In this way, an amount of change per certain time of a phase component φ (x, y, n) of the second reflected light generated by the sliced plane of the observation object 9 is determined by the analyzing unit 52 on the basis of an absolute value of an amount of change per certain time of a complex amplitude C (x, y, n) and an absolute value of the complex amplitude C (x, y, n) (that is, the intensity component R (x, y, n)), and thereby it is possible to obtain the situation of positional changes in the z direction of the reflectors in the sliced plane of the observation object 9 with respect to the respective positions (x, y).

In addition, in the case where noise superimposed on an interference figure is relatively greater than its interference component, an amount of change in the intensity component R is not made negligible. The contribution of noise appears as a Gaussian type along with its real axis component and its imaginary axis component on the complex plane. Therefore, it is possible to correct the contribution due to noise by a statistical technique. By using the following expression (16) in place of the expression (14), it is possible to provide a $\phi_{dev}$ (x, y) in the case where random noise is superimposed on an interference signal.

[Expression 16]

$$\phi_{dev}(x, y) = \frac{\sqrt{\left(\frac{1}{N - \Delta n} \sum_{n=1+\Delta n}^{N} |C(x, y, n) - C(x, y, n - \Delta n)|^2\right) - 2R_{no}^2}}{\sqrt{\left(\frac{1}{N - \Delta n} \sum_{n=1+\Delta n}^{N} |C(x, y, n)|^2\right) - R_{no}^2}} \quad (16)$$

Here, $R_{no}$ is a constant independent of coordinates denoting a magnitude of noise, which is provided by the following expression (17). However, ($x_0$, $y_0$) are the coordinates of a point considered that no significant interference signal is present in the image. For example, ($x_0$, $y_0$) may be selected as a position at which no cell is present in a sliced plane considered as being sufficiently distant from the substrate as compared with its coherence length.

[Expression 17]

$$R_{no} = \sqrt{\frac{1}{N - \Delta n} \sum_{n=1+\Delta n}^{N} |C(x_0, y_0, n)|^2} \quad (17)$$

In order to demonstrate the effectiveness of the expression (16), a simulation by the Monte Carlo method has been carried out. The simulation has been carried out such that Gaussian type noise where $R_{no}$ =1 is superimposed on C (n) where R=4 and its deflection angle changes $\phi_{dev}$ by $\phi_{dev}$. The C (n) used for the simulation is provided by the following expression (18). Here, Noise is complex Gaussian noise with the origin at the center thereof such that the real axis component and the imaginary axis component both have the standard deviation of $\frac{1}{2}^{0.5}$, which fulfills $R_{no}$=1.

[Expression 18]

$$C(n) = R(\cos(n \cdot \phi_{dev}) + i \sin(n \cdot \phi_{dev})) + \text{Noise} \quad (18)$$

In calculating under the condition of Δn=1, when no term of

Figure 18:
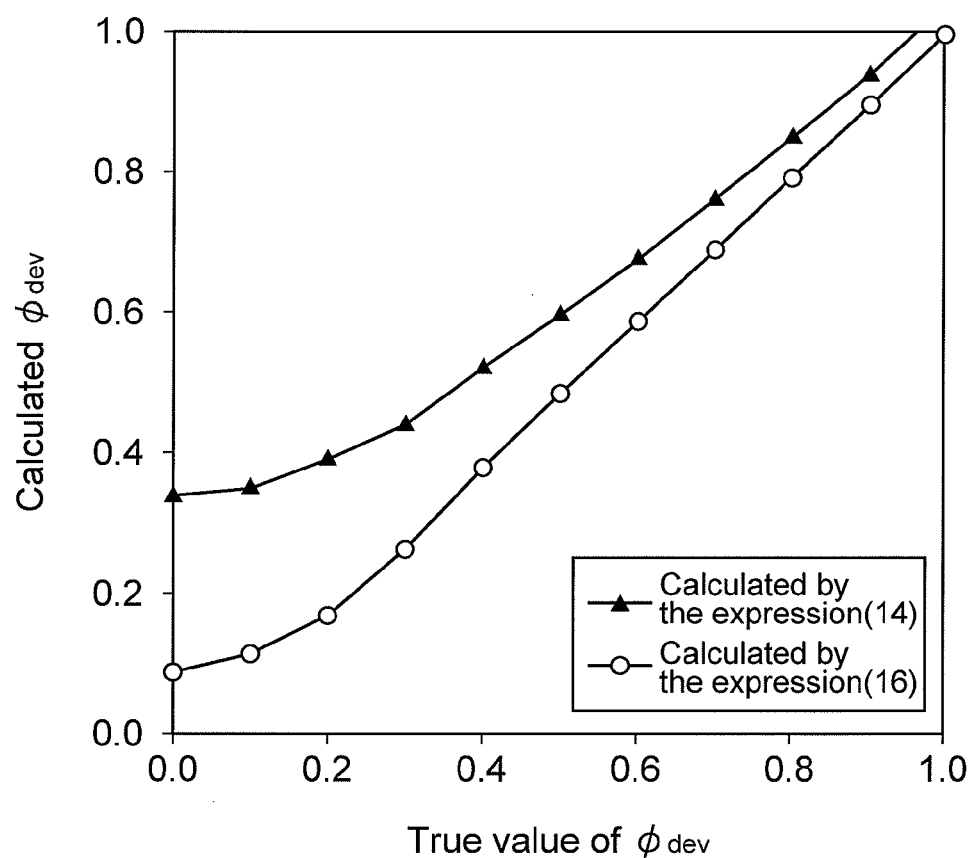
FIG. 18 is a graph showing the results of computer simulation of $\phi_{dev}$ by respective expressions (14) and (16).

Noise is present, the expression (14) always provides a true value of $\phi_{dev}$. On the other hand, when a term of Noise is present, the expression (14) goes out of a true value of $\phi_{dev}$ particularly in a region where a value of $\phi_{dev}$ is small. However, it is possible to correct the contribution of the term of Noise by using the expression (16). In the case where a term of Noise is present, $\phi_{dev}$ calculated by each of the expressions (14) and (16) is shown in FIG. 18.

In addition, in the case where an intensity component R of an interference signal is small, that is, in the case where a percentage of noise contributing to the apparent interference signal is high, the denominator of the expression (16) is extremely small or zero, which makes it impossible to precisely determine quantity $\phi_{dev}$. Therefore, by using a condition as shown in the following expression (19), for example, data on coordinates (x, y) where R of a signal is small enough to fulfill this condition are preferably not used for processing at the subsequent stage.

[Expression 19]

$$\left(\frac{1}{N-\Delta n}\sum_{n=1+\Delta n}^{N}|C(x,y,n)|^2\right)-R_{no}^2 < R_{no}^2 \quad (19)$$

The result of the analysis by the analyzing unit 52 is displayed as an image by the display unit 53. In the display unit 53, the analysis result by the analyzing unit 52 is preferably displayed as an image in gray scale, false color, or the like. By displaying it in this way, it is easy to observe the situation of the positional change in the z direction of a reflector in the sliced plane of the observation object 9.

Figure 19:
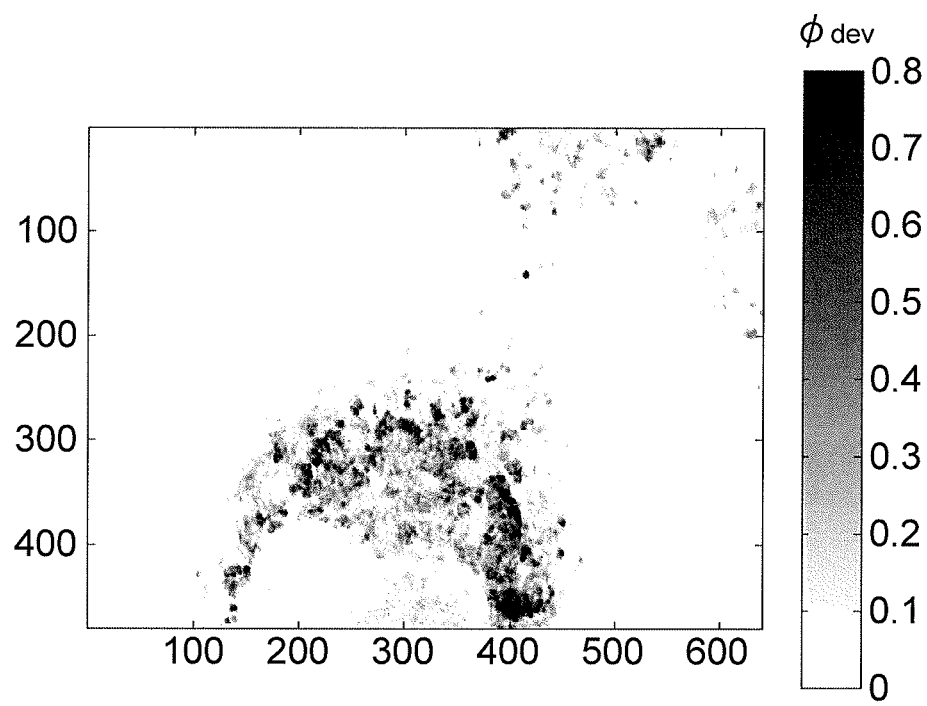
FIG. 19 is a chart showing an example of image display in a display unit 53.
Figure 20:
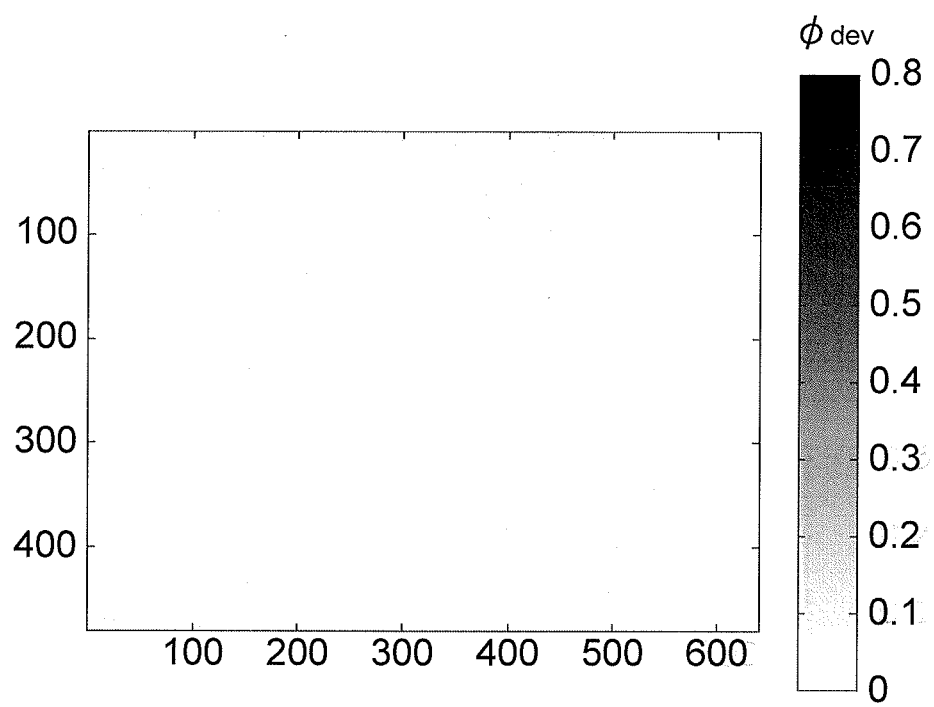
FIG. 20 is a chart showing an example of image display in the display unit 53.
Figure 21:
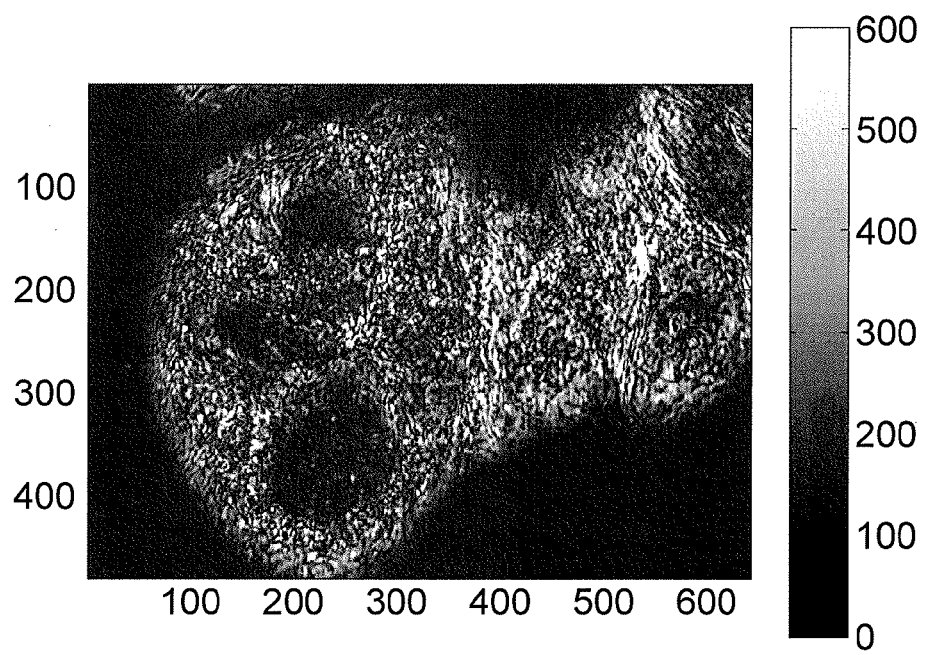
FIG. 21 is a chart showing an intensity component R (x, y) of an interference light figure.

FIGS. 19 and 20 respectively show examples of image displays in the display unit 53. The images shown in the respective FIGS. 19 and 20 are determined according to the above-described expression (16). FIG. 19 is a chart showing the image that the situation of positional changes in the z direction of the reflectors in the sliced plane of the observation object 9 is expressed in gray scale by using a live HeLa cell as the observation object 9. FIG. 20 is a chart showing the image that the situation of positional changes in the z direction of the reflectors in the sliced plane of the observation object 9 is expressed in gray scale by using a fixed HeLa cell as the observation object 9. Here, N is 66, Δn is 2, and $t_0$ is 1.2 seconds. The HeLa cell is subjected to a paraformaldehyde treatment to fix its cell membrane and its content. FIG. 21 is a chart showing an image of an intensity component R (x, y, n) of the fixed HeLa cell shown in FIG. 20.

FIGS. 19 and 20 respectively show that the higher the concentration is, the higher the motility of the reflector at that position is. As shown in FIG. 20, because the cell membrane and the content stop moving in the fixed HeLa cell, no positional changes in the z direction of the reflectors have been recognized. In contrast thereto, as shown in FIG. 19, the cell membrane and the content both move in the live HeLa cell, the positional changes in the z direction of the reflectors have been recognized.

The advantage of the technique of observing positional changes in the z direction of the reflectors according to the above-described expression (16) is in the point that there is no need to use phase unwrapping processing. The phase unwrapping is numerical processing for making discontinuous points in phase continuous, and has the possibility of causing artifact in the processing. In the above-described technique using an index $\phi_{dev}$, there is no need to use phase unwrapping, and therefore, it is possible to prevent artifact from being caused.

As described above, according to the observation device 1 according to the present embodiment or the observation method according to the present embodiment, it is possible to obtain detailed information on the observation object 9 such as a cell. Thereby, imaging of activity in a cell is possible, and it is expected that the present invention is applied to cellular study, drug discovery, regenerative medicine, and the like.

Further, it is preferable that, in the same way as described above, an amount of change per certain time of a phase component φ (x, y, n) of the second reflected light is determined by the analyzing unit 52 for each of a plurality of sliced planes of the observation object 9, and thereby it is possible to obtain the situation of positional changes in the z direction of the reflectors with respect to the respective positions (x, y). In this case, by using not only the piezoelectric actuator 71 but also the stage 81, as shown in FIG. 6 or FIG. 8, an optical path difference $\{(y_1+y_2)-(x_1+x_2)\}$ may be adjusted in a stepwise fashion. Thereafter, plural pieces of complex amplitudes C (x, y, n) may be obtained such that the phase shift amount is temporally changed as shown in FIG. 14 at each step thereof. With this, tomography observation of the observation object 9 is possible.

(Details of analysis by the analyzing unit 52 and image display by the display unit 53: Part 2)

When only the phase components φ (x, y, n) of the second reflected light are displayed as images in gray scale, false color, or the like by the display unit 53, it is possible to observe the situation of positional changes in the z direction of the reflectors in the sliced plane of the observation object 9. However, in this case, the phase components φ (x, y, n) are displayed as images in gray scale, false color, or the like regardless of the magnitude of an intensity component R (x, y, n), and therefore, a position at which an intensity component R (x, y, n) is small (that is, a position at which the reflectance of the light $\lambda_1$ is low) becomes noise. Therefore, it is difficult for a person who views an image displayed on the display unit 53 to confirm a position at which an amount of change in a phase component φ (x, y, n) is large (that is, a position at which an amount of positional changes in the z direction of the reflectors in the sliced plane of the observation object 9 is large).

Then, an intensity component R (x, y, n) and a phase component φ (x, y, n) of the second reflected light obtained by the analyzing unit 52 are displayed as images by the display unit 53 as follows. That is, the second reflected light is displayed as an image in the HSV color space by the display unit 53 such that a phase component φ (x, y, n) of the second reflected light determined by the analyzing unit 52 is reflected to hue H, and an intensity component R (x, y, n) of the second reflected light determined by the analyzing unit 52 is reflected to saturation S or value V.

Hue H in the HSV color space is a parameter showing a type of color in a range from 0 to 360. Accordingly, for example, when a phase component φ (x, y, n) can take a value in a range from −π to +π, the hue H is expressed by the expression of "360×[φ+π(x, y, n)]/2π."

Saturation S in the HSV color space is a parameter showing brilliance of color in a range from 0 to 1. Further, value V in the HSV color space is a parameter showing brightness of color in a range from 0 to 1. Accordingly, for example, by using an intensity component R (x, y, n) standardized such that its maximum value is 1, the saturation S or the value V is expressed as the standardized intensity component R (x, y, n), or expressed by the expression of "[1+R(x, y, n)/2."

The correspondence between the both is set such that the greater the intensity component R (x, y, n) is, the higher the value of the saturation S or the value V is. In the case where the intensity component R (x, y, n) is expressed with only one parameter of the saturation S or the value V, the other parameter is set to a fixed value (for example, value 1).

In this way, in the display unit 53, the second reflected light is displayed as an image in the HSV color space such that a phase component φ (x, y, n) is expressed with hue H, and an intensity component R (x, y, n) is expressed with saturation S or value V, thereby displaying the phase component φ (x, y, n) and the intensity component R (x, y, n) as a common image. With this, the saturation S or the value V is high at a position at which an intensity component R (x, y, n) is great (that is a position at which the reflectance of the light $\lambda_1$ is high), and therefore, the display of the hue H becomes stronger, and thereby the noise becomes less noticeable to a person who views the image displayed on the display unit 53. On the other hand, the saturation S or the value V is low at a position at which an intensity component R (x, y, n) is small (that is, a position at which the reflectance of the light $\lambda_1$ is low), and therefore, the display of the hue H becomes weaker, and thereby it is easy for a person who views the image displayed on the display unit 53 to confirm a position at which an amount of change in the phase component φ (x, y, n) is large (that is, a position at which an amount of positional changes in the z direction of the reflectors in the sliced plane of the observation object 9 is large).

Concrete examples of image display by the display unit 53 are as follows. In the case where an intensity component R (x, y, n) is reflected to only value V, the HSV color space is expressed by the following expression (20) with a phase component φ (x, y, n) and an intensity component R (x, y, n). In the case where an intensity component R (x, y, n) is reflected to only saturation S, the HSV color space is expressed by the following expression (21) with a phase component φ (x, y, n) and an intensity component R (x, y, n). Further, in the case where an intensity component R (x, y, n) is reflected to both of saturation S and value V, the HSV color space is expressed by the following expression (22) with a phase component φ (x, y, n) and an intensity component R (x, y, n).

[Expression 20]

$$HSV = (H, S, V) = \left(360 \times \frac{\pi + \phi(x, y, n)}{2\pi}, 1, R(x, y, n)\right) \quad (20)$$

[Expression 21]

$$HSV = (H, S, V) = \left(360 \times \frac{\pi + \phi(x, y, n)}{2\pi}, R(x, y, n), 1\right) \quad (21)$$

[Expression 22]

$$HSV = (H, S, V) \quad (22)$$
$$= \left(360 \times \frac{\pi + \phi(x, y, n)}{2\pi}, R(x, y, n), \frac{1 + R(x, y, n)}{2}\right)$$

In addition, as a comparative example, in the case where an intensity component R (x, y, n) is not reflected to any of saturation S and value V, and the both of the saturation S and the value V have a fixed value 1, the HSV color space is expressed by the following expression (23) with only the phase component φ (x, y, n) out of a phase component φ (x, y, n) and an intensity component R (x, y, n).

[Expression 23]

$$HSV = (H, S, V) = \left(360 \times \frac{\pi + \phi(x, y, n)}{2\pi}, 1, 1\right) \quad (23)$$

Figure 22:
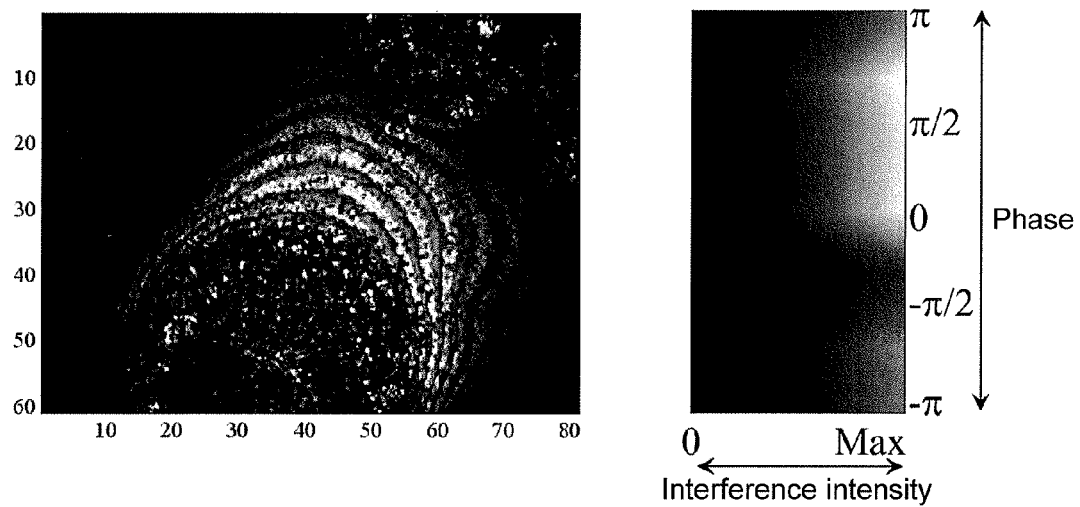
FIG. 22 is a chart showing an example of image display by the display unit 53 in the case where an intensity component R (x, y, n) is reflected to only value V (in the case of the expression (20)).
Figure 23:
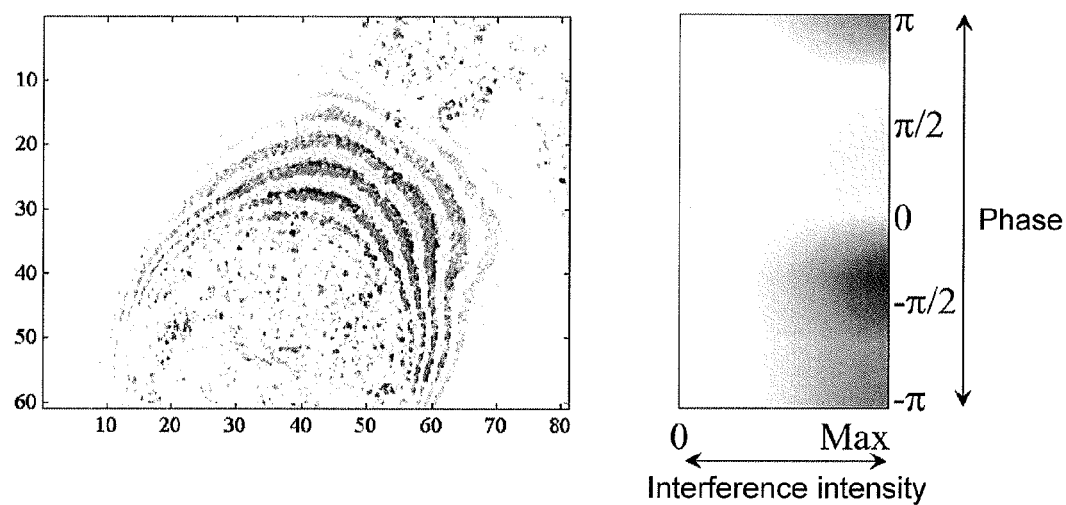
FIG. 23 is a chart showing an example of image display by the display unit 53 in the case where an intensity component R (x, y, n) is reflected to only saturation S (in the case of the expression (21)).
Figure 24:
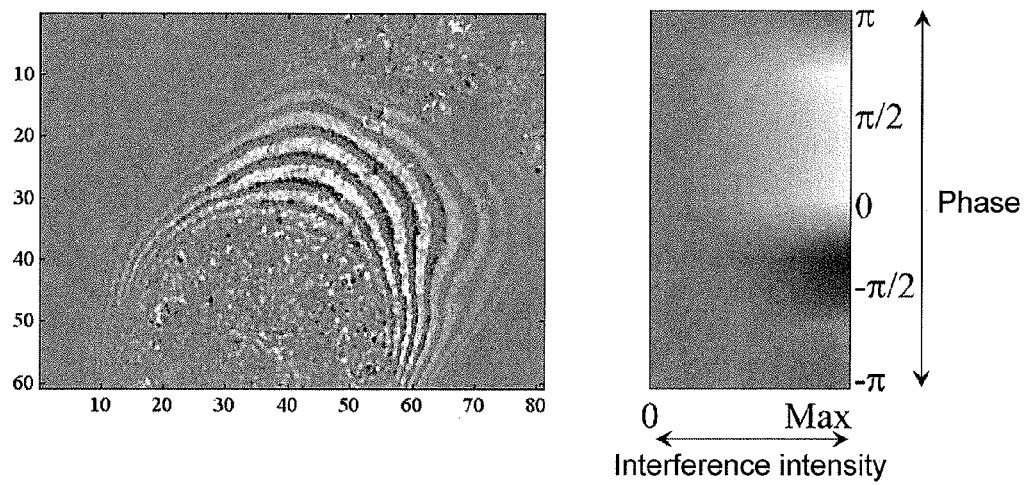
FIG. 24 is a chart showing an example of image display by the display unit 53 in the case where an intensity component R (x, y, n) is reflected to both of saturation S and value V (in the case of the expression (22)).
Figure 25:
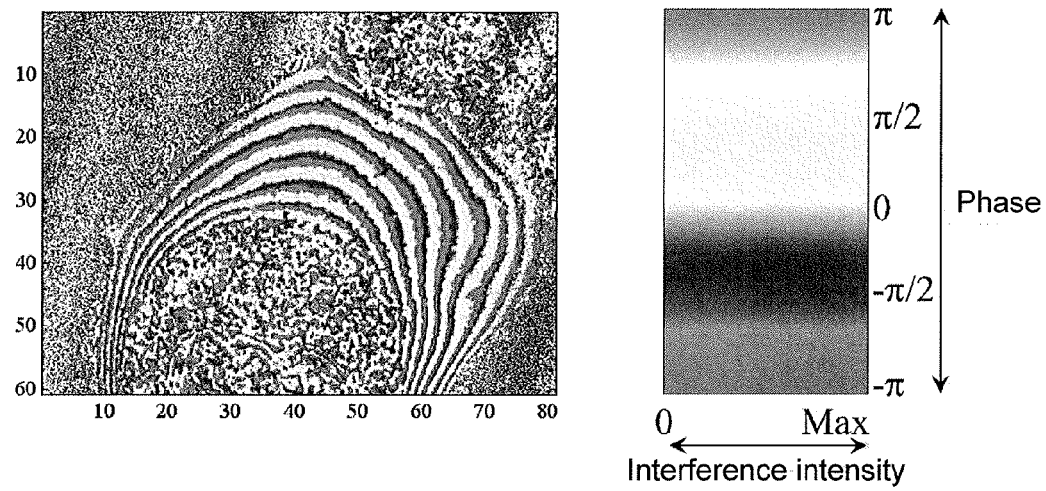
FIG. 25 is a chart showing an example of image display by the display unit 53 in the case where an intensity component R (x, y, n) is not reflected to any of saturation S and value V (in the case of the expression (23)).

FIG. 22 is a chart showing an example of image display by the display unit 53 in the case where an intensity component R (x, y, n) is reflected to only value V (in the case of the expression (20)). FIG. 23 is a chart showing an example of image display by the display unit 53 in the case where an intensity component R (x, y, n) is reflected to only saturation S (in the case of the expression (21)). FIG. 24 is a chart showing an example of image display by the display unit 53 in the case where an intensity component R (x, y, n) is reflected to both of saturation S and value V (in the case of the expression (22)). Further, FIG. 25 is a chart showing an example of image display by the display unit 53 in the case where an intensity component R (x, y, n) is not reflected to any of saturation S and value V (in the case of the expression (23)). These charts are the images which are originally displayed in false color being displayed in gray scale.

FIGS. 26 are charts shown such that the image shown in FIG. 24 (the image originally displayed in false color) is decomposed into the respective components of R, G, and B. Further, FIGS. 27 are charts shown such that the image shown in FIG. 25 (the image originally displayed in false color) is decomposed into the respective components of R, G, and B. In FIGS. 26 and 27 respectively, FIGS. 26A and 27A are the images of their R components being displayed in gray scale, FIGS. 26B and 27B are the images of their G components being displayed in gray scale, and FIGS. 26C and 27C are the images of their B components being displayed in gray scale.

In the image displays of the comparative examples (FIG. 25 and FIGS. 27), the phase component φ (x, y, n) is displayed in false color at a position at which the intensity component R (x, y, n) is small (that is, a position at which the reflectance of the light λ₁ is low), which increases noise. Therefore, it is difficult for a person who views an image displayed on the display unit 53 to confirm a position at which an amount of change in the phase component φ (x, y, n) is large (that is, a position at which an amount of positional changes in the z direction of the reflectors in the sliced plane of the observation object 9 is large).

On the other hand, in the image displays according to the present embodiment (FIGS. 22 to 24 and FIG. 26), the saturation S and the value V are high at a position at which the intensity component R (x, y, n) is great (that is, a position at which the reflectance of the light λ₁ is high). Therefore, the display of the hue H becomes stronger, and thereby the noise is not noticeable to a person who views the image displayed on the display unit 53. On the other hand, the saturation S or the value V is low at a position at which the intensity component R (x, y, n) is small (that is, a position at which the reflectance of the light λ₁ is low). Therefore, the display of the hue H becomes weaker, and thereby it is easy for a person who views the image displayed on the display unit 53 to confirm a position at which an amount of change in the phase component φ (x, y, n) is large (that is, a position at which an amount of positional changes in the z direction of the reflectors in the sliced plane of the observation object 9 is large).

As described above, according to the observation device 1 according to the present embodiment or the observation method according to the present embodiment, it is possible to obtain detailed information on the observation object 9 such as a cell to effectively display it, which makes it easy to confirm. Thereby, imaging of activity in a cell is possible, and it is expected that the present invention is applied to cellular study, drug discovery, regenerative medicine, and the like.

Further, it is preferable that, in the same way as described above, an amount of change per certain time of a phase component φ (x, y, n) of the second reflected light is determined by the analyzing unit 52 for each of a plurality of sliced planes of the observation object 9, and thereby it is possible to obtain the situation of positional changes in the z direction of the reflectors with respect to the respective positions (x, y). In this case, by using not only the piezoelectric actuator 71 but also the stage 81, as shown in FIG. 6 or FIG. 8, an optical path difference {(y₁+y₂)−(x₁+x₂)} may be adjusted in a stepwise fashion. Thereafter, plural sets of intensity components R (x, y, n) and phase components φ (x, y, n) may be obtained such that the phase shift amount is temporally changed as shown in FIG. 14 at each step thereof. With this, tomography observation of the observation object 9 is possible.

Industrial Applicability

The present invention provides an observation device and an observation method which are capable of obtaining detailed information on an object such as a cell. Further, the present invention provides an observation device and an observation method which are capable of obtaining detailed information on an object such as a cell to effectively display it.

The invention claimed is:

1. An observation device comprising:
a light source which outputs light;
an interference optical system which branches the light output from the light source into two to output as a first branched light and a second branched light, inputs a first reflected light generated due to the first branched light being reflected by a mirror, inputs a second reflected light generated due to the second branched light being reflected by a surface or an inside of an observation object, and causes the first reflected light and the second reflected light to interfere with each other to output an interference light;
an imaging optical system which images the interference light output from the interference optical system;
an image pickup unit which takes an image of an interference light figure imaged by the imaging optical system;
optical path difference adjusting means for adjusting an optical path difference between an optical path length from the light source via a reference position of the observation object up to the image pickup unit and an optical path length from the light source via the mirror up to the image pickup unit;
a control unit which controls an optical path difference adjusting operation by the optical path difference adjusting means such that the optical path difference becomes each target value in sequence; and
an analyzing unit which determines a complex amplitude of the interference light figure taken as an image by the image pickup unit with a phase shift technique after the optical path difference is set to each target value in sequence by the optical path difference adjusting means, and determines an amount of change per certain time of a phase component of the second reflected light generated on the surface or the inside of the observation object on the basis of an absolute value of an amount of change per certain time of the determined complex amplitude and an absolute value of the complex amplitude.

2. The observation device according to claim 1, further comprising a display unit which displays an image of a spatial distribution of an amount of change per certain time of a phase component of the second reflected light determined by the analyzing unit.

3. The observation device according to claim 1, wherein the analyzing unit determines an amount of change per certain time of a phase component of the second reflected light with respect to each of a plurality of sliced planes of the observation object.

4. The observation device according to claim 1, further comprising optical path difference detecting means for detecting the optical path difference, wherein the optical path difference adjusting means adjusts the optical path difference on the basis of detected results by the optical path difference detecting means.

5. The observation device according to claim 1, wherein
the optical path difference adjusting means includes first moving means for moving a first object which is one of the observation object and the mirror, and second moving means for moving a second object which is the other one of the observation object and the mirror, the optical path difference adjusting means adjusting the optical path difference by a moving operation by the first moving means or the second moving means,
the first moving means has an operating range narrower than an operating range of the second moving means, and has a positional accuracy higher than a positional accuracy of the second moving means,
the second moving means moves the second object so as to maintain the optical system between the interference optical system and the second object, and
the control unit causes a moving operation by the second moving means to be continuously or intermittently performed such that an amount of moving by the first moving means falls within a predetermined range within the operating range at each target value of the optical path difference, and performs feedback control of a moving operation by the first moving means such that the optical path difference becomes each target value even at the time of the moving operation by the second moving means.

6. An observation device comprising:
a light source which outputs light;
an interference optical system which branches the light output from the light source into two to output as a first branched light and a second branched light, inputs a first reflected light generated due to the first branched light being reflected by a mirror, inputs a second reflected light generated due to the second branched light being reflected by a surface or an inside of an observation object, and causes the first reflected light and the second reflected light to interfere with each other to output an interference light;
an imaging optical system which images the interference light output from the interference optical system;
an image pickup unit which takes an image of an interference light figure imaged by the imaging optical system;
optical path difference adjusting means for adjusting an optical path difference between an optical path length from the light source via a reference position of the observation object up to the image pickup unit and an optical path length from the light source via the mirror up to the image pickup unit;
a control unit which controls an optical path difference adjusting operation by the optical path difference adjusting means such that the optical path difference becomes each target value in sequence;
an analyzing unit which determines an intensity component and a phase component of the second reflected light generated on the surface or the inside of the observation object with a phase shift technique on the basis of the interference light figure taken as an image by the image pickup unit after the optical path difference is set to each target value in sequence by the optical path difference adjusting means; and
a display unit, which determines hue based on the phase component of the second reflected light determined by the analyzing unit and determines saturation or value based on the intensity component of the second reflected light determined by the analyzing unit, and displays an image of the second reflected light in an HSV color based on the hue and the saturation or the value.

7. The observation device according to claim 6, wherein
the analyzing unit determines plural sets of intensity components and phase components of the second reflected lights in time-series, and
the display unit displays images of these second reflected lights in time-series in the HSV color space on the basis of the plural sets of intensity components and phase components of the second reflected lights determined by the analyzing unit.

8. The observation device according to claim 6, wherein
the analyzing unit determines an intensity component and a phase component of the second reflected light with respect to each of a plurality of sliced planes of the observation object, and the display unit displays images of these second reflected lights in the HSV color space on the basis of plural sets of intensity components and phase components of the second reflected lights determined by the analyzing unit.

9. The observation device according to claim 6, further comprising optical path difference detecting means for detecting the optical path difference, wherein
the optical path difference adjusting means adjusts the optical path difference on the basis of detected results by the optical path difference detecting means.

10. The observation device according to claim 6, wherein
the optical path difference adjusting means includes first moving means for moving a first object which is one of the observation object and the mirror, and second moving means for moving a second object which is the other one of the observation object and the mirror, the optical path difference adjusting means adjusting the optical path difference by a moving operation by the first moving means or the second moving means, the first moving means has an operating range narrower than an operating range of the second moving means, and has a positional accuracy higher than a positional accuracy of the second moving means, the second moving means moves the second object so as to maintain the optical system between the interference optical system and the second object, and the control unit causes a moving operation by the second moving means to be continuously or intermittently performed such that an amount of moving by the first moving means falls within a predetermined range within the operating range at each target value of the optical path difference, and performs feedback control of a moving operation by the first moving means such that the optical path difference becomes each target value even at the time of the moving operation by the second moving means.

* * * * *